MM

US011247970B2

(12) United States Patent
Puigserver et al.

(10) Patent No.: US 11,247,970 B2
(45) Date of Patent: Feb. 15, 2022

(54) SELECTIVE INHIBITION OF GLUCONEOGENIC ACTIVITY

(71) Applicants: Dana-Farber Cancer Institute, Inc., Boston, MA (US); The Scripps Research Institute, La Jolla, CA (US); The Broad Institute, Inc., Cambridge, MA (US)

(72) Inventors: Pere Puigserver, Brookline, MA (US); Kfir Sharabi, Watertown, MA (US); Theodore Kamenecka, Palm Beach Gardens, FL (US); Patrick Griffin, Jupiter, FL (US); Stuart L. Schreiber, Boston, MA (US); Roger Schilling, Vineyard Haven, MA (US); Partha P. Nag, Somerville, MA (US); Joshua A. Bittker, Cambridge, MA (US)

(73) Assignees: Dana-Farber Cancer Institute, Inc., Boston, MA (US); The Scripps Research Institute, La Jolla, CA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 16/496,178

(22) PCT Filed: Mar. 21, 2018

(86) PCT No.: PCT/US2018/023497
§ 371 (c)(1),
(2) Date: Sep. 20, 2019

(87) PCT Pub. No.: WO2018/175537
PCT Pub. Date: Sep. 27, 2018

(65) Prior Publication Data
US 2020/0317620 A1    Oct. 8, 2020

Related U.S. Application Data

(60) Provisional application No. 62/474,861, filed on Mar. 22, 2017.

(51) Int. Cl.
| | | |
|---|---|---|
| *C07D 209/08* | (2006.01) | |
| *C07D 223/28* | (2006.01) | |
| *A61P 3/10* | (2006.01) | |
| *C07D 207/09* | (2006.01) | |
| *C07D 333/34* | (2006.01) | |
| *C07D 401/04* | (2006.01) | |
| *C07D 401/12* | (2006.01) | |
| *C07D 405/12* | (2006.01) | |
| *C07D 495/04* | (2006.01) | |
| *C07D 498/04* | (2006.01) | |
| *A61K 45/06* | (2006.01) | |

(52) U.S. Cl.
CPC .............. *C07D 223/28* (2013.01); *A61P 3/10* (2018.01); *C07D 207/09* (2013.01); *C07D 209/08* (2013.01); *C07D 333/34* (2013.01); *C07D 401/04* (2013.01); *C07D 401/12* (2013.01); *C07D 405/12* (2013.01); *C07D 495/04* (2013.01); *C07D 498/04* (2013.01); *A61K 45/06* (2013.01)

(58) Field of Classification Search
CPC ..................................................... C07D 209/08
See application file for complete search history.

(56) References Cited

U.S. PATENT DOCUMENTS

| 4,468,520 A | 8/1984 | Michel et al. | |
|---|---|---|---|
| 5,547,967 A * | 8/1996 | Kehrbach | ............ C07D 231/20 514/361 |
| 6,890,955 B2 * | 5/2005 | Hadri | .................... C07C 217/30 514/452 |
| 2007/0111998 A1* | 5/2007 | Rao | ......................... A61P 19/08 514/227.8 |
| 2011/0028719 A1* | 2/2011 | Slon-Usakiewicz | ........................ G01N 33/6896 544/177 |
| 2014/0155480 A1 | 6/2014 | Cruz et al. | |

FOREIGN PATENT DOCUMENTS

CN          104693107 A  *  6/2015

OTHER PUBLICATIONS

Tejani-Butt et al. J. Med. Chem. 1986, 29, 1524-1527 (Year: 1986).*
Goode et al. J. Med. Chem. 2008, 51, 2346-2349 (Year: 2008).*
Glushkov et al. Khimikofarmatsevticheskii Zhumal 1993, 27, 8-12 (Year: 1993).*
National Center for Biotechnology Information (2021). PubChem Substance Record for SID 292129587, SID 292129587, Source: Aurora Fine Chemicals LLC. Retrieved May 7, 2021 from https://pubchem.ncbi.nlm.nih.gov/substance/292129587, which was available Jan. 20, 2016 (Year: 2016).*
International Preliminary Report on Patentability for International Application No. PCT/US2018/023497 dated Sep. 24, 2019.
International Search Report and Written Opinion for International Application No. PCT/US18/23497 dated May 11, 2018.
Pubchem SID: 57096935, Feb. 17, 2009.
Stafylas et al., "Carvedilol in hypertension treatment," Vasc Health Risk Manag, 4(1):23-30 (2008).
Tuomilehto et al., "Prevention of type 2 diabetes mellitus by changes in lifestyle among subjects with impaired glucose tolerance," N Engl J Med, 344(18):1343-1350 (2001).

* cited by examiner

*Primary Examiner* — Matthew P Coughlin
(74) *Attorney, Agent, or Firm* — Foley Hoag LLP; DeAnn F. Smith; Janine S. Ladislaw

(57) ABSTRACT

The present invention provides compounds, pharmaceutical compositions and methods for treating and/or preventing a metabolic condition, such as diabetes.

13 Claims, 24 Drawing Sheets

SELECTIVE INHIBITION OF GLUCONEOGENIC ACTIVITY

RELATED APPLICATIONS

This application is the U.S. National Stage of International Patent Application No. PCT/US2018/23497, filed Mar. 21, 2018, which claims the benefit of priority to U.S. Provisional Patent Application Ser. No. 62/474,861, filed Mar. 22, 2017, the contents of each of which are hereby incorporated herein by reference in their entirety.

GOVERNMENT SUPPORT

This invention was made with government support under grant numbers R03 DA032468, R01 DK069966, R24 DK080261, and U54 HG005032 awarded by the National Institutes of Health. The government has certain rights in the invention.

BACKGROUND

Type 2 diabetes (T2D) has become a worldwide epidemic that affected over 400 million people in 2014 according to the World Health Organization. Uncontrolled increased blood glucose concentration is a hallmark of T2D which can lead to long term complications including micro- and macro-cardiovascular complications, neuropathy, kidney failure and increased risk for developing cancer. Maintaining blood glucose within a normal range is the foremost objective in the treatment of T2D, as this dramatically reduces the risk of developing diabetes-associated complications. Several drugs are currently being used for treatment of T2D in the clinic; these include primarily metformin, the first line drug used to treat T2D, but also sulfonylureas, thiazolidinediones (TZDs), incretin mimetics and sodium-glucose cotransporter 2 (SGLT2) inhibitors. As most patients develop resistance to metformin treatment over time, a strategy of combination therapy that includes treatment with an additional drug or insulin administration is commonly employed. This highlights the need for developing additional drugs to reduce hyperglycemia that can be used either as a monotherapy or as part of a combination therapy.

Whole body glucose homeostasis is achieved through an intricate balance between glucose production, mostly by the liver, and glucose uptake by peripheral tissues. This is regulated primarily through the opposing pancreatic hormones insulin and glucagon. In diabetic states, the liver becomes resistant to the action of insulin and produces an elevated amount of glucose which is a major contributor to the increased blood glucose levels observed in T2D. Hence, reducing HGP is a feasible strategy to manage blood glucose levels in T2D. Importantly, increased HGP in T2D was shown to be primarily a result of dysregulated gluconeogenesis rather than glycogen breakdown, suggesting that targeting components within the gluconeogenic pathway could improve hyperglycemia. Indeed, metformin is believed to exert its effect mainly by reducing hepatic gluconeogenesis.

Thus, there is a continuing need for pharmacologic agents and methods for treating and/or preventing metabolic conditions, such as T2D.

SUMMARY OF INVENTION

In one aspect, the invention relates to compounds having the structure of Formula I or a pharmaceutically acceptable salt thereof:

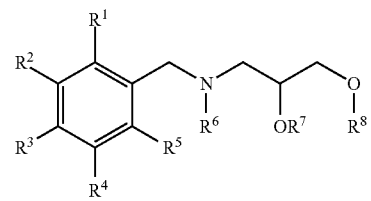

wherein $R^1$, $R^2$, $R^3$, $R^4$, $R^5$, $R^6$, $R^7$, and $R^8$ are defined herein.

In another aspect, the invention relates to pharmaceutical compositions of compounds disclosed herein and a pharmaceutically acceptable carrier.

The invention also relates to methods of treating or preventing a metabolic condition (e.g., T2D) comprising administering a compound or composition of the invention. The invention further relates to methods of modulating glucose levels in a subject comprising administering to a subject a compound or composition of the invention. In some embodiments, the methods disclosed herein include conjointly administering an additional anti-diabetic drug with the compounds disclosed herein.

The invention also relates to methods of modulating glucose release from a cell, modulating gluconeogenesis in a cell, and modulating acetylation of PGC-1α in a cell comprising contacting the cell with a compound or composition of the invention.

DETAILED DESCRIPTION OF THE INVENTION

Figure 1:
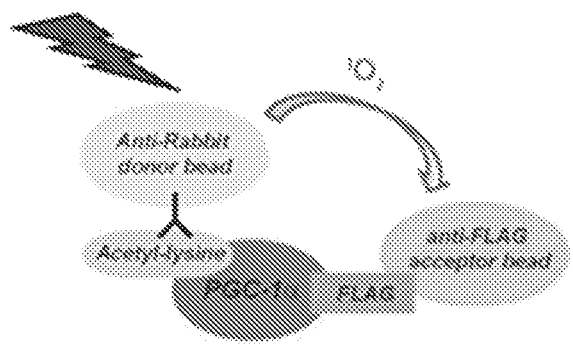
FIG. 1 is a schematic representation of the AlphaLisa assay used to detect acetylation status of PGC-1α in lysates obtained from U-2 OS cells over expressing PGC-1α and GCN5.

The transcriptional coactivator PGC-1α plays a pivotal role in energy homeostasis by co-activating transcription factors that regulate fat and glucose metabolism. As part of the fasting response, PGC-1α regulates gluconeogenesis in the liver by binding to the nuclear hormone receptors HNF4α and FoxO1 to control expression of key enzymes in the gluconeogenic pathway. PGC-1α is upregulated in several models of diabetes where gluconeogenesis is elevated, highlighting its importance in controlling blood glucose levels. While PGC-1α whole body knockout mice are able to maintain normal blood glucose levels by activating PGC-1α-independent pathways, a partial reduction in PGC-1α levels in the liver, using heterozygous knockout mice, leads to modest but significant defects in gluconeogenesis. Moreover, isolated livers from PGC-1α$^{-/-}$ mice produce less glucose compared to control mice due to reduced gluconeogenic flux from phosphoenolpyruvate, indicating that selective gluconeogenic inhibition of PGC-1α in the liver can potentially result in reduced HGP and ameliorate diabetes.

Post-translational modifications (PTMs) of PGC-1α control its transcriptional activity and metabolic function. Specifically, acetylation of multiple lysines on PGC-1α determines its ability to co-activate transcription factors involved in HGP. As part of the fasting response, SIRT1 deacetylates PGC-1α resulting in enhancement of its activity and increased glucose production. The acetyl transferase GCN5, on the other hand, catalyzes acetylation of PGC-1α reducing expression of gluconeogenic genes and glucose output. In addition, as part of the response to feeding and insulin, the Cyclin D1/Cdk4 complex phosphorylates GCN5 to induce its activity and inhibit gluconeogenic gene expression. Another node of the insulin response that regulates the activity of PGC-1α during the re-feeding response involves Akt, S6K and Clk2, which phosphorylate PGC-1α on its SR domain to inhibit its activity and reduce HGP. Hence, specific manipulation of PGC-1α PTMs can be a potential way to control its gluconeogenic activity to improve hyperglycemia.

Accordingly, in certain aspects, disclosed herein are various novel compounds, and pharmaceutical compositions thereof and methods of using the compounds to treat or prevent a metabolic condition (e.g., T2D). The compounds disclosed herein reduce fasting blood glucose, significantly increase hepatic insulin sensitivity and improve glucose homeostasis ameliorating diabetes in dietary and genetic mouse models.

I. COMPOUNDS

In certain embodiments, the invention relates to compounds having the structure of Formula (I), or a pharmaceutically acceptable salt thereof:

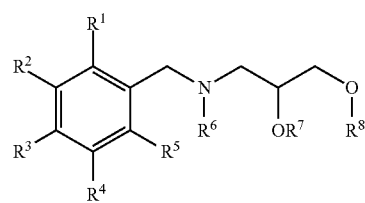

I wherein
each of $R^1$, $R^2$, $R^3$, $R^4$, and $R^5$ are independently H, halo, optionally substituted alkyl, optionally substituted cycloalkyl or optionally substituted alkoxy;
$R^6$ is H, optionally substituted alkyl or optionally substituted cycloalkyl;
$R^7$ is H or optionally substituted alkyl;
$R^8$ is optionally substituted heterocyclyl, aryl, or heteroaryl;
provided that the compound is not

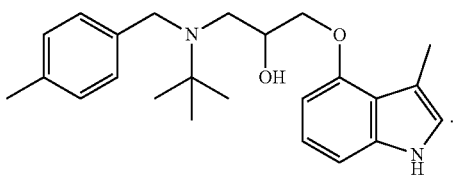 [SMILES: Cc1ccc(CN(CC(O)COc2cccc3[nH]cc(C)c23)C(C)(C)C)cc1]

In some embodiments, $R^1$, $R^2$, $R^3$, $R^4$, and $R^5$ are independently H, halo, optionally substituted lower alkyl (e.g., methyl, ethyl, propyl), or optionally substituted lower alkoxy (e.g., methoxy, ethoxy, propoxy).

In some embodiments, $R^3$ is halo (e.g., F).

In some embodiments, $R^6$ is methyl, ethyl, n-propyl, iso-propyl, n-butyl, sec-butyl, tert-butyl, pentyl, hexyl, pentyl, cyclopropyl, cyclobuytl, cyclopentyl, or cyclohexyl, preferably iso-propyl, tert-butyl, or cyclopropyl.

In some embodiments, $R^7$ is H.

In certain embodiments, $R^8$ is optionally substituted heteroaryl (e.g., indolyl) In certain embodiments, $R^8$ is

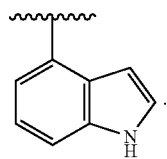 [SMILES: *c1cccc2[nH]ccc12]

In certain embodiments, $R^8$ is optionally substituted aryl (e.g., phenyl).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. The compounds of the invention have more than one stereocenter. Consequently, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, as will be described in detail below, the present invention relates to methods of treating or preventing a metabolic condition with a compound of Formula I, or a pharmaceutically acceptable salt thereof. In certain embodiments, the therapeutic preparation may be enriched to provide predominantly one enantiomer of a compound of one of Formula I. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the present invention provides a pharmaceutical preparation suitable for use in a human patient in the treatment of a metabolic condition, comprising an effective amount of any compound of one of Formula I, and one or more pharmaceutically acceptable excipients. In certain embodiments, the pharmaceutical preparations may be for use in treating or preventing a condition or disease as described herein.

Compounds of any of the above structures may be used in the manufacture of medicaments for the treatment of any diseases or conditions disclosed herein.

Exemplary compounds of the invention are depicted in Tables 1 and 2. The compounds of Table 1 and 2 are understood to encompass both the free base and the conjugate acid. For example, the compounds in Table 1 may be depicted as complexes or salts with trifluoroacetic acid or hydrochloric acid, but the compounds in their corresponding free base forms or as salts with other acids are equally within the scope of the invention. Compounds may be isolated in either the free base form, as a salt (e.g., a hydrochloride salt) or in both forms. In the chemical structures shown below, standard chemical abbreviations are sometimes used.

TABLE 1

Exemplary Compounds

| Structure | Compound Name |
|---|---|
| 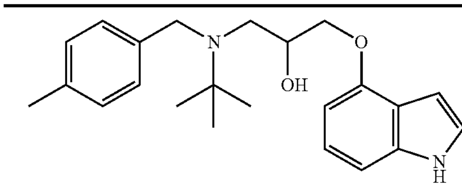 | SR-18292 |
| 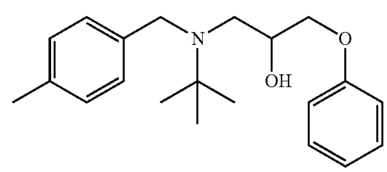 [SMILES: Cc1ccc(CN(CC(O)COc2ccccc2)C(C)(C)C)cc1] | SR-19138 |
| 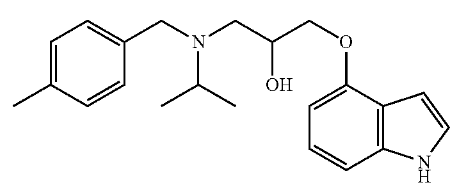 [SMILES: Cc1ccc(CN(CC(O)COc2cccc3[nH]ccc23)C(C)C)cc1] | SR-19140 |
| 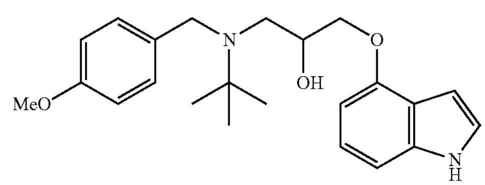 [SMILES: COc1ccc(CN(CC(O)COc2cccc3[nH]ccc23)C(C)(C)C)cc1] | SR-19141 |

TABLE 1-continued
Exemplary Compounds
| Structure | Compound Name |
|---|---|
| 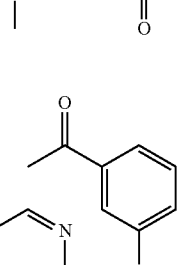 | SR-19142 |
| 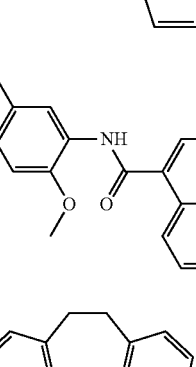 | SR-19143 |
| 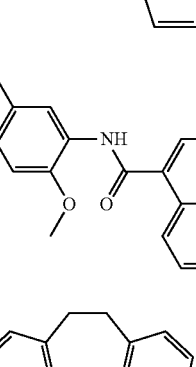 | SR-19144 |
| 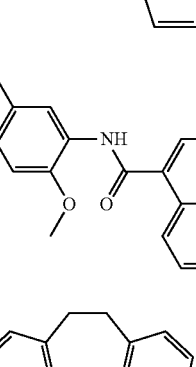 | SR-19146 |
TABLE 2
Additional Compounds of the invention
| Structure | Compound Name |
|---|---|
| 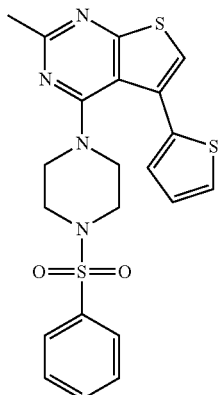 | C-82 |
TABLE 2-continued
Additional Compounds of the invention
| Structure | Compound Name |
|---|---|
| 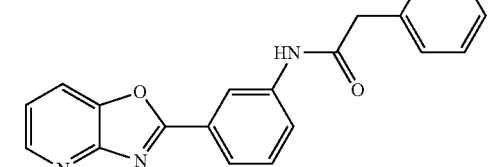 | C-79 |
| 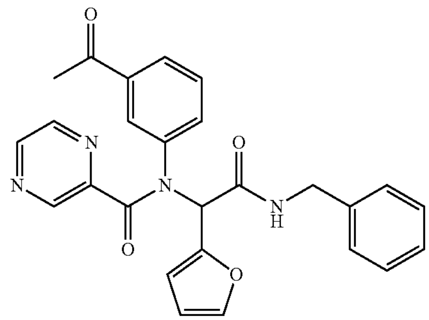 [SMILES: CC(=O)c1cccc(N(C(=O)c2cnccn2)C(C(=O)NCc2ccccc2)c2ccco2)c1] | C-983 |
| 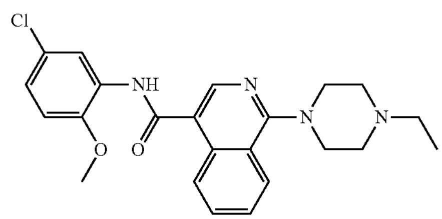 [SMILES: CCN1CCN(c2ncc(C(=O)Nc3cc(Cl)ccc3OC)c3ccccc23)CC1] | C-984 |
| 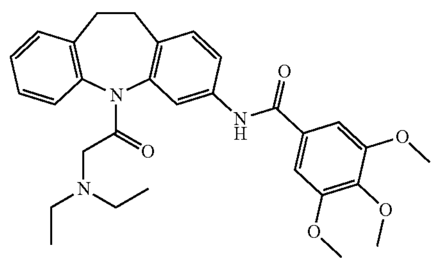 [SMILES: CCN(CC)CC(=O)N1c2ccccc2CCc2ccc(NC(=O)c3cc(OC)c(OC)c(OC)c3)cc21] | C-457 |
| 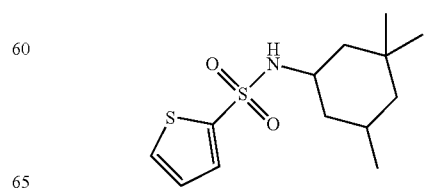 | C-975 |
| 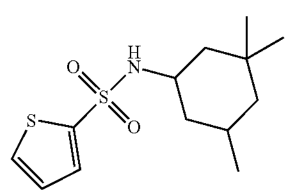 [SMILES: CC1CC(NS(=O)(=O)c2cccs2)CC(C)(C)C1] | C-18 |

TABLE 2-continued

Additional Compounds of the invention

| Structure | Compound Name |
|---|---|
| 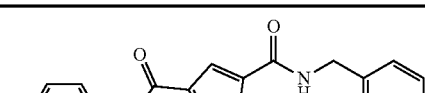 | C-981 |
| 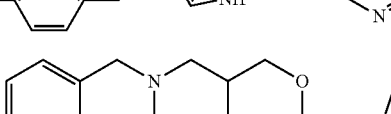 | C-80 |

II. PHARMACEUTICAL COMPOSITIONS

In certain embodiments, the present invention provides pharmaceutical compositions comprising a compound of one of Formula I and a pharmaceutically acceptable carrier. In certain other embodiments, the present invention provides pharmaceutical compositions comprising a compound of Table 2 and a pharmaceutically acceptable carrier. In some embodiments, the composition further comprises one or more anti-diabetic drug.

The compositions and methods of the present invention may be utilized to treat a subject in need thereof. In certain embodiments, the subject is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In some embodiments, the compositions and combinations of the present invention comprise at least one compound of Formula (I), or a pharmaceutically acceptable salt thereof, and one or more anti-diabetic drugs. In some embodiments, the compositions and combinations of the present invention comprise at least one compound of Table 2, or a pharmaceutically acceptable salt thereof, and one or more anti-diabetic drugs.

In certain embodiments, compounds of the invention may be used alone or conjointly administered with another type of therapeutic agent (e.g., an anti-diabetic drug). As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional anti-diabetic drug(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

Examples of anti-diabetic drugs include, but are not limited to, sulfonyl ureas, meglitinides, biguanides, thiazolidinediones, alpha glucosidase inhibitors, incretin mietics, DPP-IV (dipeptidyl peptidase-4 or DPP-4) inhibitors, amylin analogues, insulin (including insulin by mouth), Sodium-glucose Cotransporter-2 (SGLT2) Inhibitors, and herbal extracts.

Non-limiting examples of sulfonylureas include tolbutamide (Orinase®), acetohexamide (Dymelor®), tolazamide (Tolinase®), chlorpropamide (Diabinese®), glipizide (Glucotrol(RO), glyburide (Diabeta®, Micronase®, and Glynase®), glimepiride (Amaryl®), and gliclazide (Diamicron®).

Non-limiting examples of meglitinides include repaglinide (Prandin®), and mateglinide (Starlix®).

Non-limiting examples of biguanides include metformin (Glucophage®).

Non-limiting examples of thaizolidinediones, also known as glitazines, include rosiglitazone (Avandia®), pioglitazone (Actos®), and troglitazine (Rezulin®).

Non-limiting examples of gludosidase inhibitors include miglitol (Glyset®) and acarbose (Precose/Glucobay®).

Non-limiting examples of Sodium-glucose Cotransporter-2 (SGLT2) inhibitors include canagliflozin, dapagliflozin, and empagliflozin.

Non-limiting examples of incretin mimetics include GLP agonists such as exenatide and exendin-4, marketed as Byetta® (Amylin Pharmaceuticals, Inc. and Eli Lilly and Company.) Non-limiting examples of Amylin analogues include pramlintide acetate (Symlin® Amylin Pharmaceuticals, Inc.).

Non-limiting examples of DPP4 inhibitors and other anti-diabetic drugs include the following: sitagliptin (marketed as Januvia®, available from Merck, pyrazine-based DPP-IV derivatives such as those disclosed in WO-2004085661, bicyclictetrahydropyrazine DPP IV inhibitors such as those disclosed in WO-03004498, PHX1149 (available from Phenomix, Inc.), ABT-279 and ABT-341 (available from Abbott, see WO-2005023762 and WO-2004026822), ALS-2-0426 (available Alantos and Servier), ARI 2243 (available from Arisaph Pharmaceuticals Inc., U.S. Ser. No. 06/803,357 and U.S. Ser. No. 06/890,898), boronic acid DPP-IV inhibitors such as those described in U.S. patent application Ser. No. 06/303,661, BI-A and BI-B (available from Boehringer Ingelheim), xanthine-based DPP-IV inhibitors such as those described in WO-2004046148, WO-2004041820, WO-2004018469, WO-2004018468 and WO-2004018467, saxagliptin (Bristol-Meyers Squibb and Astra Zenica), Biovitrim (developed by Santhera Pharmaceuticals (formerly Graffinity)), MP-513 (Mitsubishi Pharma), NVP-DPP-728 (qv) and structurally related 1-((S)-gamma-substituted prolyl)-(S)-2-cyanopyrrolidine compounds and analogs of NVP-DPP-728 (qv), DP-893 (Pfizer), vildagliptin (Novartis Institutes for BioMedical Research Inc), tetrahydroisoquinoline 3-carboxamide derivatives such as those disclosed in U.S. patent application Ser. No. 06/172,081, N-substituted 2-cyanopyrrolidines, including LAF-237, such as those disclosed in PCT Publication Nos. WO-00034241, WO-00152825, WO-02072146 and WO-03080070, WO-09920614, WO-00152825 and WO-02072146, SYR-322 (Takeda), denagliptin, SNT-189546, Ro-0730699, BMS-2, Aurigene, ABT-341, Dong-A, GSK-2, HanAll, LC-15-0044, SYR-619, Bexel, alogliptin benzoate, and ALS-2-0426 Non-limiting examples of other anti-diabetic drugs includemetformin, thiazolidinediones (TZD), and sodium glucose cotransporter-2 inhibitors such as dapagliflozin (Bristol Meyers Squibb) and sergliflozin (GlaxoSmithKline), and FBPase (fructose 1,6-bisphosphatase) inhibitors.

III. USES OF COMPOUNDS AND COMPOSITIONS

In certain aspects, the invention provides methods of treating or preventing a metabolic condition comprising administering to a subject a compound or a composition disclosed herein. In some embodiments, the metabolic condition is diabetes mellitus (e.g., Type I, Type II, gestational diabetes).

In certain aspects, the invention further provides methods of modulating glucose levels in a subject comprising administering to a subject a compound or a composition disclosed herein.

In some embodiments, the methods disclosed herein further comprise administering an anti-diabetic drug to the subject.

In certain embodiments, the subject is a mammal, e.g., a human.

The invention also provides methods of modulating glucose release from a cell comprising contacting the cell with a compound or composition disclosed herein. In some embodiments, disclosed are methods of modulating gluconeogenesis in a cell comprising contacting the cell with a compound or composition disclosed herein. In certain other aspects, the invention provides methods of modulating acetylation of PGC-1α in a cell comprising contacting the cell with a compound or composition disclosed herein. In some embodiments, the cell is a hepatocyte or a pancreatic cell. Such methods disclosed herein may be performed in vivo or in vitro.

IV. DEFINITIONS

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, —OCF$_3$, ethoxy, propoxy, tert-butoxy and the like.

The term "cycloalkyloxy" refers to a cycloakyl group having an oxygen attached thereto.

The term "alkoxyalkyl" refers to an alkyl group substituted with an alkoxy group and may be represented by the general formula alkyl-O-alkyl.

The term "alkylaminoalkyl" refers to an alkyl group substituted with an alkylamino group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

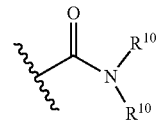

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

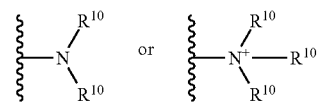

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

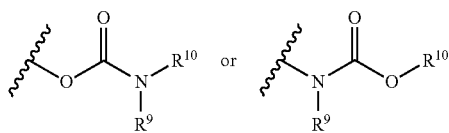

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle"

includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The term "heteroalkylamino", as used herein, refers to an amino group substituted with a heteralkyl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, benzimidazole, quinoline, isoquinoline, quinoxaline, quinazoline, indole, isoindole, indazole, benzoxazole, pyrazine, pyridazine, purine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocycloalkyl", as used herein, refers to an alkyl group substituted with a heterocycle group.

The term "heterocycloalkylamino", as used herein refers to an amino group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

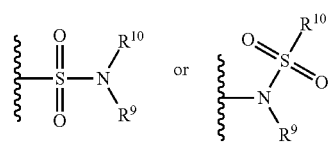

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

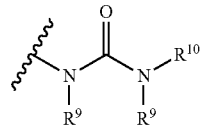

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of one of Formulas I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of one of Formulas I in a formulation represented above can be replaced with the corresponding suitable prodrug, e.g., wherein a hydroxyl in the parent compound is presented as an ester or a carbonate or carboxylic acid present in the parent compound is presented as an ester.

V. EXAMPLES

The invention now being generally described, it will be more readily understood by reference to the following examples which are included merely for purposes of illustration of certain aspects and embodiments of the present invention, and are not intended to limit the invention.

Example 1—General Biochemistry Methods

Animal Procedures.

All mice were purchased from Jackson laboratories and housed under a 12 h light/12 h dark cycle at 22° C. Before handling, mice were allowed to acclimate for at least 1 week in our animal facility. For in vivo studies with DIO mice, males 6-8 weeks old were fed HFD for the indicated time. For drug administration, SR-18292 was re-suspended in a 10% DMSO/10% Tween80/80% PBS solution at a final concentration of 6-12 mg/ml. Metformin was re-suspended in the same solution at a 20 mg/ml concentration. SR-18292 was injected via I.P. for 3 days between 4-5 pm and food was removed on day 3 at 5 pm. The following morning (day 4) SR-18292 was injected again (for a total of 4 injections) and blood glucose was measured after 3 hours. Injection volume did not exceed 275 µl per mouse. Metformin was administered via oral gavage. Pyruvate tolerance and glucose tolerance tests were performed following the same dosing protocol, but 3 hours after the last injection mice were injected with either pyruvate (2 g/Kg) or glucose (2 g/kg or 0.5 g/kg for Lep$^{ob/ob}$) and blood glucose was measured every 20 minutes. Insulin tolerance test was performed following the same dosing protocol, but mice were fasted for 4 hours after the forth injection before performing the test. Insulin was injected via I.P. (0.5 U/Kg) and blood glucose was measured every 20 minutes. Glycemia was measured by tail bleed using a glucometer (OneTouch). For all experiments, age- and body weight-matched animals were used. For protein, RNA extracts and biochemistry studies, livers were removed following each experiment and snap frozen in liquid nitrogen. For information on number of animals in each experiment please refer to FIGS. 4, 5 and S5 legends.

All studies were performed according to protocols approved by Beth Israel Deaconess Medical Center's Animal Care and Use Committee.

Primary Hepatocytes and Cell Cultures.

U-2 OS cell lines were maintained in DMEM containing 10% FBS. Transfections were performed with Polyfect (QIAGEN) with a fixed total quantity of DNA. Cells were collected after 24 h or 48 h of transfection as indicated. Medium was changed every day as well as 3 h before collecting cells. Primary hepatocytes were isolated from 8- to 12-week-old male C57BL/6 mice by perfusion with liver digest medium (Invitrogen, 17703-034) followed by 70 µm mesh filtration. Percoll (Sigma, P7828) gradient centrifugation allowed primary hepatocytes isolation from other cell types and debris. Cells were seeded in plating medium (DMEM with 10% FBS, 2 mM sodium pyruvate, 1% penicillin/streptomycin, 1 µM dexamethasone, and 100 nM insulin). After 4 h of seeding, the medium was changed and incubated overnight in maintenance medium (DMEM, 0.2% BSA, 2 mM sodium pyruvate, 1% penicillin/streptomycin, 0.1 µM dexamethasone, and 1 nM insulin). To infect cells, the indicated adenoviruses were added at MOI of 2.5 to 5 for 4 h. Cells were collected within 48 h after infection and medium was changed every day.

Primary and Secondary AlphaLisa Screen to Determine Single Dose and Dose Response Effects on PGC-1α Acetylation.

U-2 OS cells were thawed and grown in 4 Triple flasks (NUNC) with growth medium. After 48 hours, cells were harvested and seeded in 4 Hyper flasks at a density of 15-20 million cell each. Cells were then grown for 4-5 days until reached confluency. After reaching the desired confluency, medium was changed to assay medium and cells were infected with Ad-PGC-1α and Ad-GCN5 for 4 hours. Following infection, medium was changed to phenol-free medium and cells were incubated overnight. The following day, cells were harvested and seeded on a 384-well plate at 7000 cells/well in 50 ml assay media. Cells were allowed to adhere for 4-8 hours after which 100 nl of compound was added. After overnight incubation with compound, media was aspirated and cells were incubated with lysis buffer for 1 hour at RT. For detection of acetylated PGC-1α, cells were incubated with 6 ml of Acetyl-Lys antibody for 1 hour at RT. Lysates were then incubated with Alpha acceptor beads (6 ml, 1 hour RT) and Alpha donor beads (6 ml, 1 hour RT). Perkin Elmer EnVision plate reader was used for signal detection using Alpha protocol. For each compound, activity score was calculated based on the mean of the normalized and corrected sample activity replicates. Compounds with activity score≥50 (50% activity above neutral control) were called as hits. As a positive control, each plate contained wells that were treated with fascaplysin, a CDK4 inhibitor, that reduces the acetylation of PGC-1α. For a compound to be called a hit all replicates had to be considered hits. Active hits from primary screen were then used in a secondary screen to determine $AC_{50}$ toward PGC-1α acetylation. Same protocol for detection of PGC-1α acetylation was applied but compounds were added at different doses. For each sample the highest valid tested concentration was determined and set as Maximum concentration. Raw signals of the plate wells were normalized using the 'Neutral Controls Minus Inhibitors' method in Genedata Assay Analyzer (v10.0.2). AC values were calculated using the curve fitting strategies in Genedata Screener Condoseo (7.0.3) and up to the active concentration limit (Maximum concentration) described for each sample.

High Throughput Cytotoxicity Panel.

To determine potential cytotoxicity of identified compounds 3 different cell lines were used (HEK293, HepG2 and A549). Cells were grown in Triple flask to reach ~95% confluence and then re-suspended for dispensing at 50,000 cells/mL of medium (DMEM, 10% FBS, Penicillin/Strep/L-Glutamine). The following day, cells were plated on 384-well plates in 40 ml medium and incubated for 24 hours in standard tissue culture conditions. Compounds (100 nl) were then added at different doses into 40 ml assay volume and incubated for 72 hours. To determine cell viability, plates were removed from the incubator and allowed to cool down for 15 minutes and viability was determined by addition of 20 ml 50% Promega CellTiterGlo (diluted 1:1 with PBS, pH 7.4) and incubation at RT for 5 minutes. PerkinElmer EnVision was used to measure luminescence.

High Throughput qPCR Screen.

To determine the effects of compounds on expression level of Pck1 and G6pc genes, primary hepatocytes were isolated as described herein. Following isolation, hepatocytes were seeded in 384-well plates at 4000 cells/well in 40 ml plating medium and incubated overnight at 37° C. The next morning, plating media was aspirated and 40 ml maintenance medium (DMEM, 5% FBS, 2 mM sodium pyruvate, 1% Pen/Strep, 1 nM insulin, 0.1 mM dexamethasone) was added. Incubation at 37° C. was continued until afternoon when compounds were added (100 nl) at dose using 384 well pin tool on pin table (Walkup Cybi Well). After overnight incubation, maintenance medium was aspirated and low serum medium was added (DMEM, 5% FBS, 2 mM sodium pyruvate, 1% Pen/Strep). Compounds were re pinned to cells and plates were returned to incubator for additional 3 hours. After 3 hours forskolin stimulation started for additional 1.5 hours. For cDNA synthesis Cells-to-Ct kit (Ambion, 4391851C) was used. The medium was aspirated and cells were washed twice (100 mL with PBS) using the ELX405 Plate washer (Biotek). The assay plates were flipped upside down and centrifuged at 1000 rpm 2 minutes to remove the excess liquid. 10 μL of Lysis solution with DNase I (from Cell to CT Lysis kit, Ambion) was added to each well using the MultiDrop Combi/Standard tube dispensing cassette (Thermo Scientific). Each assay plate was then shaken for 2 minutes and incubated for an additional 8 minutes at RT. At the end of the incubation, 1 μL of stop solution was added with the Multidrop Combi-nl (Thermo Scientific) and the assay plates were centrifuged (face up) (1000 rpm, 2 minutes). The assay plates were incubated for 2 minutes at RT and processed for reverse transcription. For reverse transcription, 8 μL of RT master mix (RT buffer, RT Enzyme mix, $H_2O$) was dispensed into each well of a RT assay plate (Axygen, PCR-384 RGD C). 2 μL of the lysed cells were transferred into RT assay plate using Vario transfer unit (CyBi Well). The RT assay plates were incubated at 37° C. for 1 h and the reverse transcriptase is inactivated by incubating the plates for 1 minute at 95° C. qPCR assay was performed by the addition of 4 ml/well of PCR master mix (Roche) to PCR plate (Roche Light Cycler 480 MultiWell Plate 384, Cat #04 729 749 001) using the Multidrop Combi-nl (Thermo Scientific). 1 μL/well of RT DNA is then transferred to the 4 μL/well PCR plate using CyBi Well. The PCR plates were centrifuged (face up) for 2 minutes at 1000 rpm. PCR was performed using Thermo-Cycler (Roche Light Cycler 480 II) with Macro Probe Protocol (95° C. for 10 min, 55 cycles of 95° C. for 10 sec, 60° C. for 30 sec and 40° C. for 30 sec). TaqMan probe sets that were used (Mouse Pck1, Applied Biosystems, 4351370 (Mm01247058_m1), Mouse G6pc, Applied Biosystems, 4351370 (Mm00839363_m1), mouse Gapdh, Applied Biosystems (4352339E)). To calculate inhibitory $AC_{50}$, dose response curves were generated by determining the difference in Ct values between compound treatment and forskolin control at each dose and were fit to the Hill equation. Curves were forced through 100% inhibitory activity (which was determined to be the DMSO control), so as to generate $AC_{50}$ values calculated based on these curve, that were comparable between compounds. This was done even if in some cases higher inhibition than the DMSO control was observed. AC values were calculated using the curve fitting strategies in Genedata Screener Condoseo (7.0.3).

Drug Treatment of Primary Hepatocytes for Measurement of Protein Modification, Gene Expression and Glucose Output.

For measurement of acetylation, gene expression and glucose production SR-18292 (20 mM) was added to cells overnight and fresh compound was added the following day for additional 3 h before collecting the cells (for total of ~18 h treatment). Where insulin and glucagon stimulation were performed, the medium was changed to starvation medium (DMEM, 0.2% BSA, 2 mM sodium pyruvate, and 1% penicillin/streptomycin) with fresh compound for the last 3 h and cells were stimulated with either 100 nM insulin or 200 nM glucagon for an extra 1.5 h. For glucose measurements following PGC-1α over expression cells were incubated for the last 3 h in glucose-free medium (phenol-red/glucose free DMEM, 0.2% BSA, 2 mM sodium pyruvate and 20 mM sodium lactate or 10 mM glycerol in case glycerol was used as substrate). For glucose measurements following glucagon stimulation cells were incubated for the last 4 h in the same glucose-free medium that also contained glucagon (200 nM). The glucose level in the medium was measured using a glucose assay kit from Eton Bioscience Inc. by adding 50 ml of assay buffer to 50 ml of medium followed by 15 min incubation at 37° C. Absorbance was measured at 490 nm.

DNA Constructs and Adenoviruses.

Adenoviruses were produced with the pAd-Track/pAd-Easy system. FLAG-HA-PGC-1α and FLAG-GCN5 adenoviruses were made as previously described (Lerin et al., 2006; Rodgers et al., 2005). FLAG-HA-PGC-1α, FLAG-GCN5 pcDNA 3.1 constructs were made as previously described (Lerin et al., 2006; Rodgers et al., 2005). shLacZ was cloned into the BLOCK-iT™ U6 RNAi Entry Vector Kit (Thermo Fisher Scientific) and subsequently cloned into the pAd/BLOCK-iT™ RNAi vector. shPGC-1α was produced using the pAd-Track/pAd-Easy system.

siRNA Mediated Knock Down of Ppargc1a.

siRNA oligos against mouse Ppargc1a were purchased from OriGene (SR420231). Hepatocytes were transfected with a 1:1:1:mixture of 3 unique 27mer siRNA duplexes (20 mM each) using Lipofectamin RNAiMax (Invitrogen) immediately upon seeding with plating medium. The following morning cells were washed with PBS and medium was changed to maintenance medium. In the afternoon, cells were transfected again and compound treatment started.

Cell Lysis and Immunoprecipitation.

For PGC-1α acetylation detection in hepatocytes cells were infected with Ad-PGC-1α and Ad-GCN5. Cells were collected in RIPA buffer (containing protease inhibitor cocktail, 5 mM NaF, 5 mM β-glycerophosphate, 10 mM nicotinamide, 1 mM DTT and 1 μM trichostatin A). FLAG-HA-PGC-1α was immunoprecipitated overnight at 4° C. with FLAG beads (Sigma A2220). For GCN5 interaction with PGC-1α, U-2 OS cells were infected with Ad-PGC-1α. Nuclear extracts were obtained by lysing cell in Buffer A (10 mM HEPES-KOH (pH 7.9), 10 mM KCl, 1.5 mM $MgCl_2$, 0.5 mM DTT, 0.25% IGEPAL (v/v), 5 mM NaF, 5 mM β-glycerophosphate, 5 mM sodium butyrate and 10 mM nicotinamide), supplemented with Protease Inhibitor Cocktail. Once cytoplasmic fractions were separated, nuclear pellets were lysed in Buffer B (20 mM HEPES-KOH (pH 7.9), 125 mM NaCl, 1 mM EDTA, 1 mM DTT, 1% IGEPAL (v/v), 10% glycerol (v/v), 5 mM NaF, 5 mM β-glycerophosphate, 5 mM sodium butyrate and 10 mM nicotinamide), supplemented with Protease Inhibitor Cocktail. FLAG-HA-PGC-1α was immunoprecipitated with FLAG beads overnight at 4° C. All beads were washed at last 3 times in lysis buffer before eluting in sample loading buffer.

Quantitative Real-Time PCR Analysis.

Total RNA was extracted from cells or pulverized liver using TRIzol reagent (Ambion, Life Technologies), followed by cDNA preparation from 2 μg of total RNA with a High-Capacity cDNA Reverse Transcription Kit (Applied Biosystems). cDNA products were quantified by real-time PCR using Power SYBR Green PCR Master Mix (Applied Biosystems) on a CFX384 Real-Time PCR System (Bio-Rad). To calculate $IC_{50}$ from C-80 dose response, curves were fit to the hill equation in a similar manner used to calculate estimated $AC_{50}$ from the high-throughput qPCR screen. However, unlike the curves from the qPCR high-throughput screen, values of relative repression were used rather than of delta-Ct.

Transcriptional Reporter Assays.

U-2 OS cells were transfected with a fixed amount of DNA. After 6 h medium was changed and compound treatment started. The following morning medium was changed again and fresh compound was added for additional 3 h after which cells were collected (24 h post transfection) with 1× Passive Lysis Buffer (Promega). Firefly luciferase reporter was determined by addition of Luciferase Assay Substrate (Dual-Luciferase Reporter Assay System, Promega) and quantification of luminescence on a FLUOstar Omega plate reader (BMG Labtech). CMV-driven *Renilla* luciferase vector was cotransfected as an internal control. Data are presented as firefly luciferase reporter values normalized to *Renilla* values and are representative of at least two independent experiments.

Chromatin Immunoprecipitation.

Primary hepatocytes were fixed in 1% formaldehyde for 10 minutes at room temperature. Crosslinking was quenched by adding glycine to a final concentration of 125 mM and rinsing twice with PBS. Cells were collected in PBS containing protease inhibitors followed by lysis in chromatin immunoprecipitation (ChIP) buffer (50 mM HEPES pH, 7.9; 140 mM NaCl; 1 mM EDTA; 1% Triton X-100; 0.1% NaDOC, 0.1% sodium dodecyl sulfate (SDS) and protease inhibitors). Chromatin was sheared by sonication with a Diagenode Biorupter for three cycles of 5 minutes (30 seconds on, 30 seconds off). Samples were clarified and chromatin immunoprecipitated overnight at 4° C. with the indicated antibody. Immune complexes were recovered with Protein A magnetic beads (Dynabeads; Novex, Life Technologies) preblocked with salmon sperm DNA (Invitrogen, Life Technologies). Following extensive washes, immunoprecipitated DNA was then isolated with a Chelex. Input DNA was prepared from 10% of respective chromatin prior to precipitation. Immunoprecipitated DNA and input DNA were analyzed by quantitative real-time PCR with primers specific for the indicated region.

Adenovirus Injection to Mice.

Virus was introduced to mice through the tail vein injection. Virus was thawed before injection and the desired amount of virus was diluted with saline to a final volume of 100 μL per mouse. Each mouse was injected with $6*10^7$ pfu/g. SR-18292 treatment started on day 5 post infection.

Hyperinsulinemic-Euglycemic Clamp Studies.

Hyperinsulinemic-euglycemic clamps were performed on mice fed HFD for 16 weeks as previously described with minor modifications (Jurczak et al., 2012). Briefly, an indwelling catheter was surgically implanted in the right jugular vein 7 days prior to study. Three days before study, mice were injected with SR-18292 and vehicle control following the same protocol described above. Mice were fasted overnight prior to clamps and then infused with a fixed amount of insulin [4 mU/(kg-min)] and a variable amount of 20% dextrose to maintain euglycemia. [3-H] glucose was included in the infusate to allow for the calculation of whole-body rates of glucose metabolism.

GCN5 Activity Assay.

For determination of GCN5 HAT activity U-2 OS cells overexpressing Ad-GCN5 were treated with SR-18292 (10 mM) for 18 h. Cells were lysed with buffer B (20 mM HEPES-KOH (pH 7.9), 125 mM NaCl, 1 mM EDTA, 1 mM DTT, 1% IGEPAL (v/v), 10% glycerol (v/v), 5 mM NaF, 5 mM β-glycerophosphate, 5 mM sodium butyrate and 10 mM nicotinamide), supplemented with Protease Inhibitor Cocktail. FLAG-GCN5 was immunoprecipitated with FLAG beads overnight at 4° C. following multiple washes with lysis buffer. GCN5 was then eluted using 3×FLAG peptide and the purified protein was used to determine HAT activity using the HAT Inhibitor Screening Assay Kit (Cayman Chemicals) per manufacturer instructions. To determine the potential effect of SR-18292 on GCN5 activity in vitro, GCN5 was purified from U-2 OS cells in a similar manner but without treatment with SR-18292.

Mass Spectrometry.

Gel bands were dehydrated with acetonitrile, dried and resuspended in 50 mM ammonium bicarbonate (pH 8.0) containing 500 ng of sequencing-grade trypsin (Promega) and incubated at 37° C. for 8 hours. Digested samples were then loaded onto StageTips and desalted. Peptides were eluted with 50% acetonitrile, 5% formic acid, dried using a Speed-Vac apparatus, and resuspended in 25 μl of HEPES, pH 8.5. Peptides were labeled with 6-plex tandem mass tag (TMT) reagents (Thermo Scientific, Rockford, Ill.). After 1 hour of incubation at room temperature, the reaction was quenched with hydroxylamine and acidification with formic acid to pH~2. TMT labeled peptides were combined, desalted by StageTips, dried and resuspended in 10 μl of 1% formic acid. All spectra were acquired using an Oribtrap Fusion mass spectrometer (Thermo Scientific) in line with an Easy-nLC 1200 (Thermo Fisher Scientific) ultra-high pressure liquid chromatography (UHPLC) pump. TMT labeled peptides (4 μl) were separated onto a 75 μM inner diameter column containing 1 cm of Magic C4 resin (5 μm, 100 Å, Michrom Bioresources) followed by 35 cm of Sepax Technologies GP-C18 resin (1.8 μm, 120 Å) with a gradient consisting of 4-30% (ACN, 0.125% FA) over 90 min at ~250 nl/min. For all LC-MS/MS experiments, the mass spectrometer was operated in the data-dependent mode where the MS1 spectra was set at a resolution of 120,000, with an AGC target of 150,000 and a max injection time of 100 ms. The ten most intense ions were selected for MS2. MS1 precursor ions were excluded using a dynamic window (60 seconds+/− 10 ppm) and the MS2 precursors were isolated with a quadrupole mass filter set to a width of 0.5 DA. For MS3 based TMT quantitation, MS2 spectra were collected at an AGC of 4000, max injection time of 150 ms, and CID collision energy set at 35%. MS3 spectra were acquired in the Orbitrap parameters where the HCD collision energy was increased to 55%. Synchronous-precursor-selection (SPS) was enabled to include up to six MS2 fragment ions for the MS3 spectrum. A compendium of in-house software was used to convert raw files to mzXML format that adjusted monoisotopic m/z measurements and corrected erroneous peptide charge state assignments. Assignment of MS2 spectra was performed using the SEQUEST algorithm. All searches utilized the human UniProt database (downloaded Jun. 10, 2016) where reversed protein sequences and known contaminants (keratins, etc.) were included. SEQUEST searches were performed using a 10 ppm precursor ion tolerance and requiring each peptide's N/C terminus to have tryptic specificity and allowing up to three missed cleavages. TMT tags on lysine residues and the N-terminus (+229.162932 Da) was set as static modifications as well, while methionine oxidation (+15.99492 Da) and acetylation on lysine (−187.1523673 DA) was set as variable modifications. An MS spectra assignment false discovery rate (FDR) of less than 1% was achieved by applying the target-decoy database search strategy 3 and acetylated peptides were also manually validated. For quantification, a 0.03 m/z window centered on the theoretical DA value of each reporter ion was utilized for the nearest maximal signal intensity. Reporter ion intensities were adjusted to correct for the isotopic impurities from the different TMT reagents as per manufacturer's specifications. The signal to noise values for all peptides for PGC-1α were summed within each TMT channel and all acetylated peptides were normalized to that PGC-1α summed signal. For each peptide, a total minimum sum signal to noise value of 200 and an isolation purity greater than 70% was required.

Serum and Liver Biochemistry Measurements.

Serum samples were gathered from blood collected by cardiac puncture. Insulin was measured with Ultra Sensitive Mouse Insulin ELISA Kit (Crystal Chem, 90080). Kits used to measure alanine transaminase (EALT-100), aspartate transaminase (EASTR-100), lactate dehydrogenase (DLDH-100) were purchased from Bioassay Systems. Kits used to measure lactate (MAK 064), b-hydroxybutyrate (MAK 041), Triglycerides (TR0100) were purchased from Sigma. Kit used to measure cholesterol (C7510) was purchased from Pointe Scientific. Kit used to measure non-esterified fatty acids was purchased from Wako.

Cytotoxicity Determination in Primary Hepatocytes.

For cell viability determination using MTT, primary hepatocytes were seeded on a 96-well plate at 20,000 cells/well. The following day cells were treated at different doses, as indicated, for 18 h following similar protocol described above for drug treatment of primary hepatocytes. 5 ml of MTT reagent (5 mg/ml) was then added to each well (n=4/dose) and cells were incubated for 1 h at 37° C. Medium was discarded and dye was extracted by adding 100 ml DMSO to each well. For cytotoxicity determination using ToxiLight Non-destructive Cytotoxicity Bioassay, hepatocytes were seeded on a 6-well plate and treated with either SR-18292 (20 mM) or cisplatin (50 mM) for 18 h. 50 ml of medium was collected and used to measure cellular toxicity by adding 100 of adenylate kinase detection reagent (AKDR) and incubating 5 min at RT before measuring luminescence.

Quantification and Statistical Analysis

Data were analyzed using Prism software (GraphPad Software, Inc.) and are expressed as mean±SEM. Two-tailed Student t tests, one-way ANOVA with either Tuckey or Dunnet or Two-way ANOVA with Sidak comparison test were used to compare means between groups as indicated; P<0.05 was considered significant

TABLE 3

A list of primers used for qPCR analysis

| Gene | Forward primer (5'-3') | Reverse primer (5'-3') |
| --- | --- | --- |
| Ppargc1a | TCC TCC TCA TAA AGC CAA CC | GCC TTG GGT ACC AGA |
| Pck1 | CAT ATG CTG ATC CTG GGC ATA AC | CAA ACT TCA TCC AGG |
| G6pc | ACA CCG ACT ACT ACA GCA ACA G | CCT CGA AAG ATA GCA |
| SREBP1c | CGT CTG CAC GCC CTA GG | CTG GAG CAT GTC TTC |
| Fasn | CGG AAA CTT CAG GAA ATG TCC | TCA GAG ACG TGT CAC |
| ACC1 | CAT CTA TTT TTG ATG TCC TAC CAA ACT TC | ACG CTG TTA AGT TCA TAG GCA ATA |
| CD36 | GGC CAA GCT ATT GCG ACA T | CAG ATC CGA ACA CAG |
| ElovL6 | TCG AAC TGG TGC TTA CAT GC | TGC ATA AGC CCA GAA |
| MCAD | GAA GGT TGA ACT CGC TAG GC | GCT AGC TGA TTG GCA |
| Acox1 | CCT GAT TCA GCA AGG TAG GG | TCG CAG ACC CTG AAG |
| CPT2 | GAA GAA GCT GAG CCC TGA TG | GCC ATG GTA TTT GGA |
| Tnf | CCC TCA CAC TCA GAT CAT CTT CT | GCT ACG ACG TGG GCT |
| IL6 | CTG CAA GAG ACT TCC ATC CAG | AGT GGT ATA GAC AGG |
| ifng | GCT TTG CAG CTC TTC CTC AT | GTC ACC ATC CTT TTG |
| Tgfb1 | TGC GCT TGC AGA GAT TAA AA | AGC CCT GTA TTC CGT |
| Ccl2 | GCT CTC TCT TCC TCC ACC AC | GCG TTA ACT GCA TCT |
| Ccl7 | CCT GGG AAG CTG TTA TCT TCA | AGG CAC ATT TCT TCA |
| IL1b | GCT CTT GTT GAT GTG CTG CTG | TTT GAC AGT GAT GAG |

Example 2—Exemplary Synthetic Protocols for Compounds of Formula I

Procedures for Chemical Synthesis of SR-18292

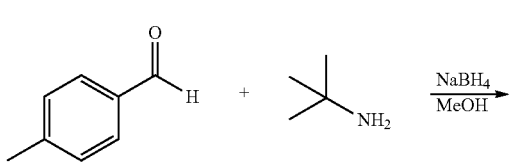

-continued

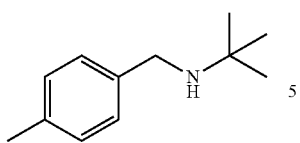

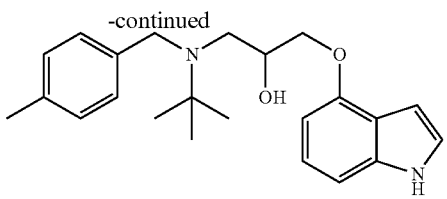

To a room temperature solution of 4-methylbenzaldehyde (2 g, 16.65 mmol) in MeOH (25 mL) was added 2-methyl-propan-2-amine (1.217 g, 16.65 mmol). The solution was stirred at room temperature for 1 hour, cooled to 0° C., and then treated with NaBH$_4$ (1.260 g, 33.3 mmol) in one portion. The reaction mixture was allowed to warm to room temperature overnight with stirring. The reaction was quenched with saturated aqueous NH$_4$Cl solution and extracted with ethyl acetate. The organic layer was washed with saturated sodium bicarbonate solution, brine, dried (Na$_2$SO$_4$) and concentrated under reduced pressure. The crude residue was purified by flash chromatography on silica gel (EtOAc/hexanes) to give 2-methyl-N-(4-methylbenzyl)propan-2-amine (2.42 g, 13.65 mmol, 82% yield) as white solid. HRMS (ESI$^+$), m/z: [M+H]$^+$, calcd. for $C_{12}H_{20}N^+$ 178.1590; found 178.1598.

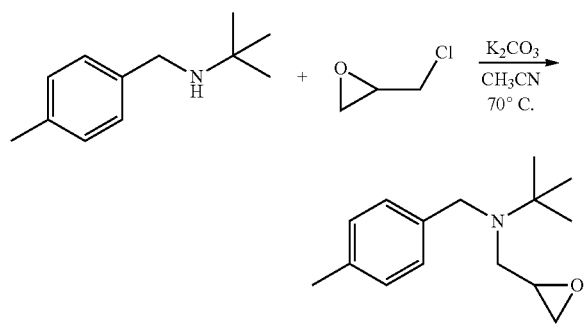

To a solution of 2-methyl-N-(4-methylbenzyl)propan-2-amine (2.42 g, 13.65 mmol) in acetonitrile (25 mL) was added 2-(chloromethyl)oxirane (2.53 g, 27.3 mmol), K$_2$CO$_3$ (3.77 g, 27.3 mmol) and KI (4.53 g, 27.3 mmol). The mixture was heated to 70° C. for 16 h, cooled, and filtered, washing with ethyl acetate. The filtrate was concentrated in vacuo and purified by flash chromatography on silica gel (EtOAc/hexanes) to afford 2-methyl-N-(4-methylbenzyl)-N-(oxiran-2-ylmethyl)propan-2-amine (2.1 g, 9.0 mmol, 66% yield) as colorless oil. $^1$H NMR (400 MHz, CDCl$_3$) δ 1.17 (s, 9H), 2.33 (s, 3H), 3.60 (d, J=14.8 Hz, 1H), 3.83 (d, J=14.8 Hz, 1H), 7.09 (t, J=3.0 Hz, 1H), 7.10 (d, J=7.8 Hz, 2H), 7.28 (d, J=7.9 Hz, 2H). HRMS (ESI$^+$), m/z: [M+H]$^+$, calcd. for $C_{15}H_{24}NO^+$ 234.1852; found 234.1862.

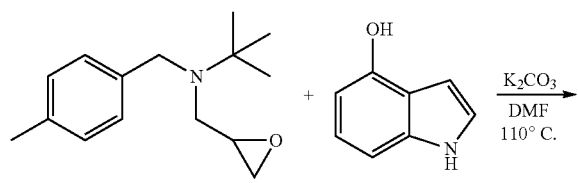

To a solution of 2-methyl-N-(4-methylbenzyl)-N-(oxiran-2-ylmethyl)propan-2-amine (100 mg, 0.43 mmol) in DMF (2 ml) was added 1H-indol-4-ol (114 mg, 0.86 mmol) and K$_2$CO$_3$ (119 mg, 0.86 mmol). The mixture was heated to 110° C. for 16 h and then cooled. The reaction mixture was diluted with ethyl acetate, washed with saturated sodium bicarbonate solution, brine, dried (Na$_2$SO$_4$) and concentrated in vacuo. The residue was purified by reverse-phase preparative HPLC to give 1-((1H-indol-4-yl)oxy)-3-(tert-butyl(4-methylbenzyl)amino)propan-2-ol (TFA salt, 55 mg, 0.11 mmol, 27% yield) as colorless solid. $^1$H NMR (400 MHz, CDCl$_3$) δ 1.21 (s, 9H), 2.33 (s, 3H), 2.80-2.95 (m, 2H), 3.30 (br, 1H), 3.57-3.63 (m, 2H), 3.83-3.95 (m, 3H), 6.39 (d, J=7.5 Hz, 1H), 6.62 (t, J=3.1 Hz, 1H), 7.00 (d, J=7.3 Hz, 1H), 7.05 (d, J=7.4 Hz, 1H), 7.09 (t, J=3.0 Hz, 1H), 7.13 (d, J=7.8 Hz, 2H), 7.24 (d, J=8.0 Hz, 2H), 8.19 (brs, 1H). HRMS (ESI$^+$), m/z: [M+H]$^+$, calcd. for $C_{23}H_{31}N_2O_2^+$ 367.2380; found 367.2398.

Figure 2:
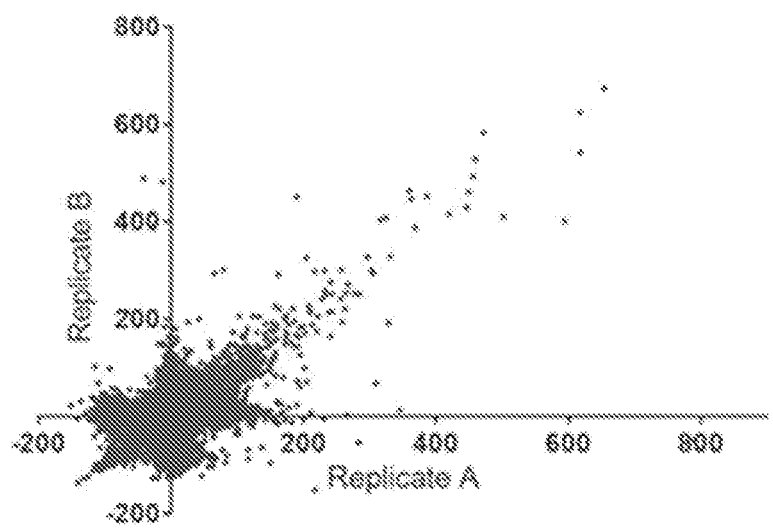
FIG. 2 is a scatter plot of primary screen results. A total of 741 compounds that induced acetylation signal by ≥50% compared to control were identified and considered active. Axes represent activity score.
Figure 3:
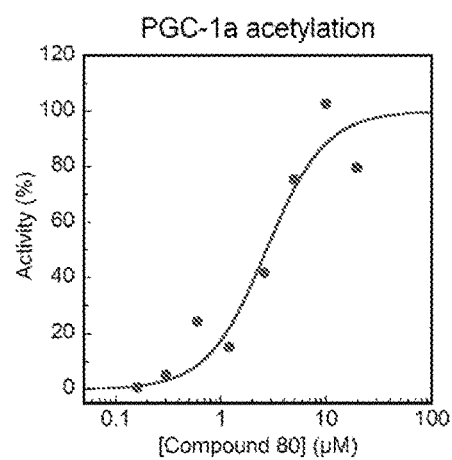
FIG. 3 is a plot of the dose response curve of lead compound (C-80). The effect of the primary screen hits on PGC-1α acetylation was re-tested in a dose response manner.
Figure 32:
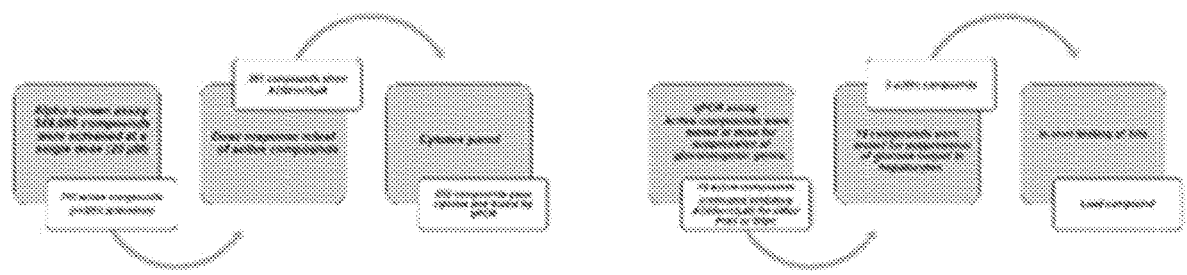
FIG. 32 is a schematic showing the work flow of screen starting with a high-throughput AlphaLisa screen through secondary screens.
Figure 33:
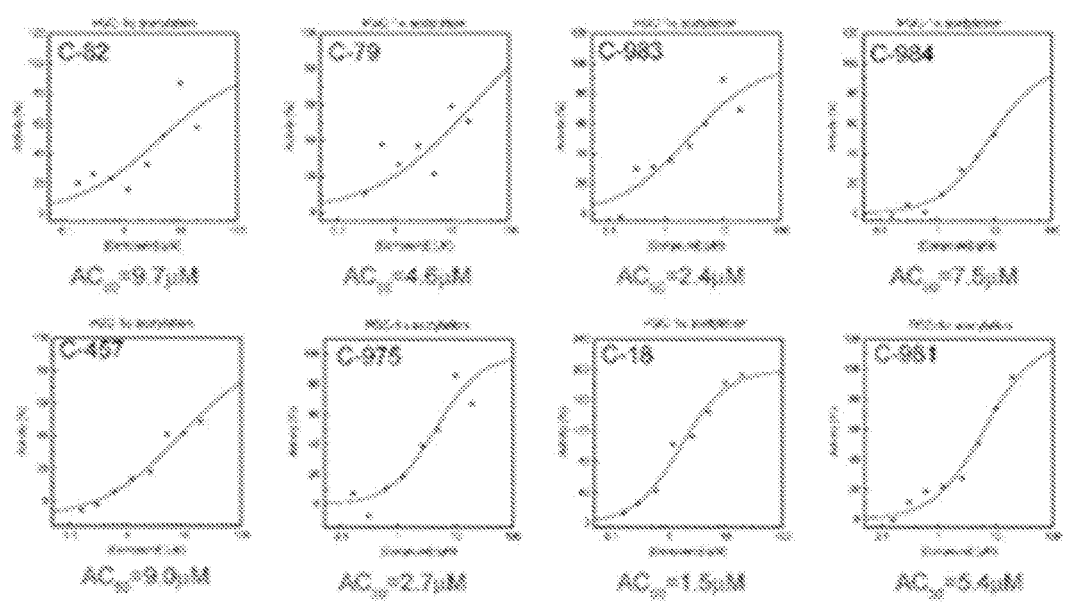
FIG. 33 depicts the dose response acetylation curves of final hits presented in FIG. 5.

Example 3—an AlphaLisa Cell-Based High-Throughput Chemical Screening Platform Identifies Small Molecules that Increase PGC-1α Acetylation and Suppress HGP To identify novel anti-diabetic chemical probes that increase PGC-1α acetylation and subsequently inhibit its gluconeogenic activity, a cell-based high-throughput chemical screening platform was designed. The MLP (NIH Molecular Library Probes) and DOS (Diversity-Oriented Synthesis) chemical libraries, totaling ~350,000 compounds, were screened using the U-2 OS cell line transiently co-expressing PGC-1α and GCN5. An AlphaLisa assay was developed to quantify changes in PGC-1α acetylation upon single dose treatment with each compound from these libraries (FIG. 1). Using this platform, changes in PGC-1α acetylation could be measured and 741 active compounds were identified which increased the lysine acetylation signal over 50% compared to vehicle control (FIG. 2). These compounds were considered positive hits from the primary screen. To further winnow our hit list, these compounds were re-tested at dose using the same assay. Based on the potency to increase PGC-1α acetylation (AC50 of <10 μM) (FIGS. 3, 32 and 33), 381 compounds were selected. Next, a cytotoxicity assay was applied to triage compounds that were toxic to HEK293, HepG2 and A549 cells. As a result, 252 non-toxic compounds were chosen for secondary screening assays.

Figure 4:
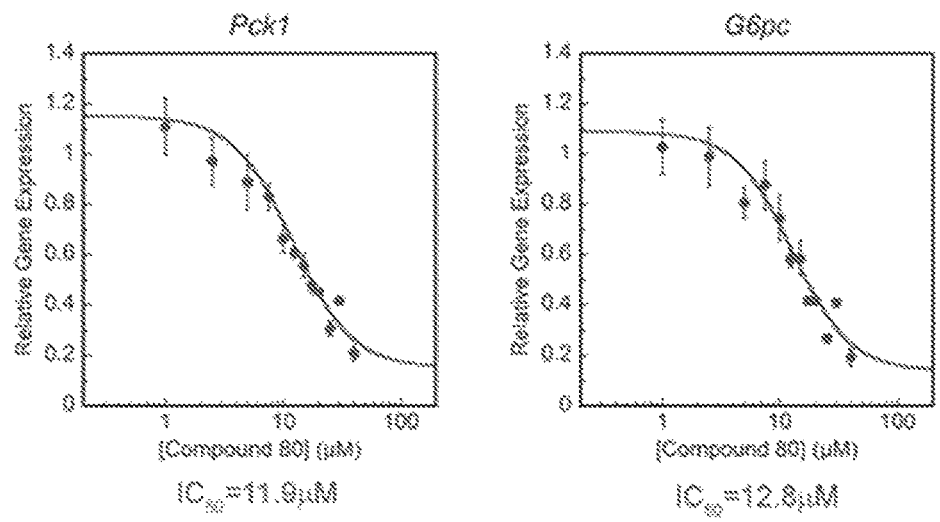
FIG. 4 includes two plots of the relative gene expression for Pck1 and G6pc. Isolated mouse primary hepatocytes were used to determine the effect of remaining hits on Pck1 and G6pc gene expression (see also FIG. 34). Forskolin was used to induce Pck1 and G6pc expression (considered as 100% activation) and cells were treated with each compound at dose. Data was fit to the Hill equation to calculate estimated $AC_{50}$.
Figure 5:
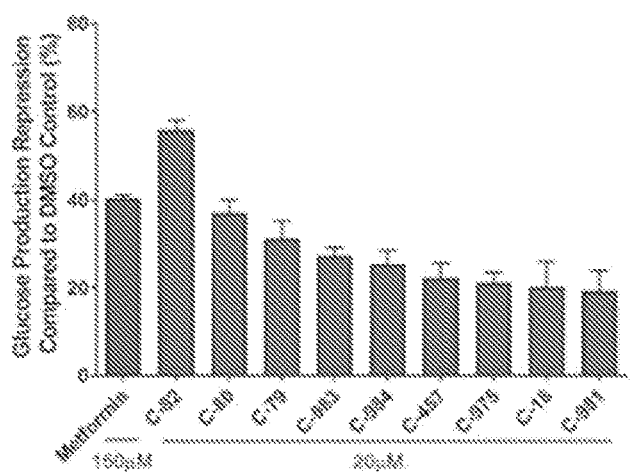
FIG. 5 is a bar graph showing repression of glucose production from hepatocytes following treatment with various compounds of the invention. Hepatocytes were infected with Ad-PGC-1α and Ad-GCN5 to induce glucose production. Cells were treated overnight with an overall of 19 compounds, that were identified in the qPCR assay. Pyruvate/lactate were used as substrates for glucose production. Compounds that significantly reduced glucose levels in the medium compared to DMSO control are presented.
Figure 34:
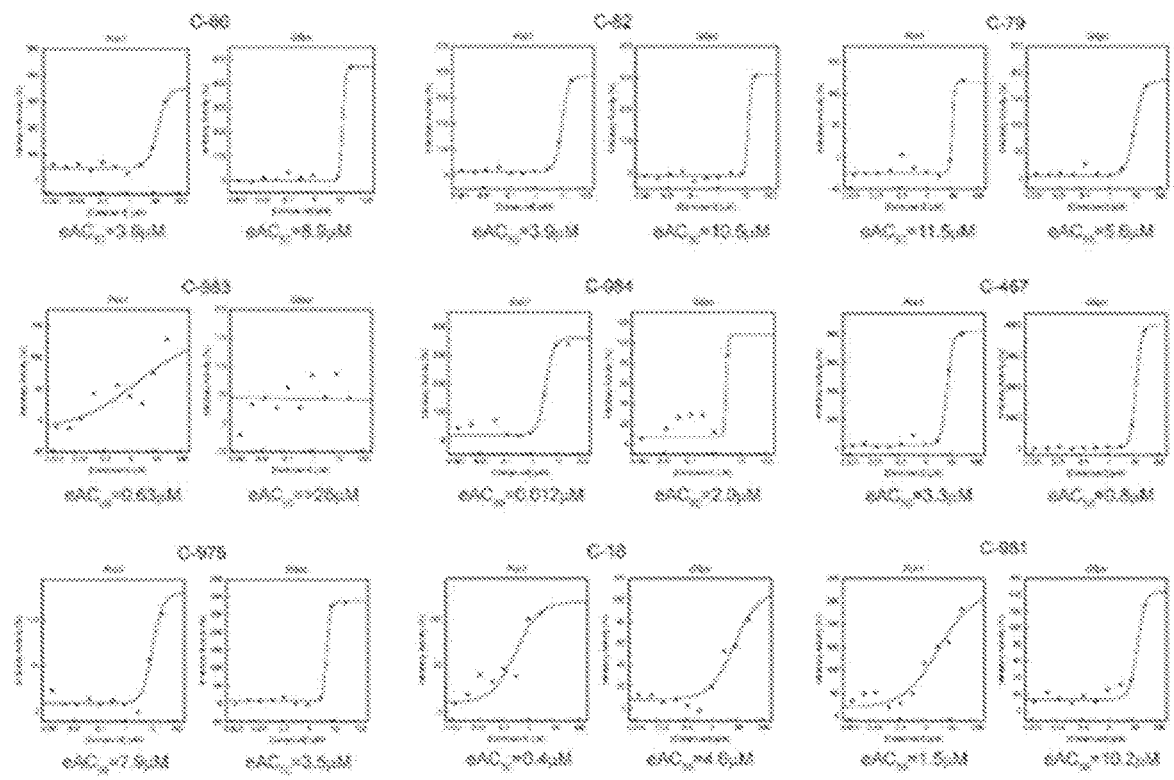
FIG. 34 depicts the dose response curves showing estimated inhibitory activity toward Pck1 and G6pc gene expression following forskolin treatment. To calculate estimated inhibitory $AC_{50}$ values ($eAC_{50}$) that were comparable between compounds, curves were forced through 100% inhibitory activity (which was determined to be the DMSO control). $AC_{50}$ were calculated as described in herein.

PGC-1α activates hepatic gluconeogenic gene expression, and an increase in its acetylation status reduces expression of both Pck1 and G6pc genes (Rodgers et al., 2005; Yoon et al., 2001). It was predicted that a set of the selected 252 positive small molecule hits would suppress gluconeogenic gene expression in primary hepatocytes. Thus, a high-throughput screen with these 252 compounds at different doses was performed. Briefly, Hepatocytes were treated with forskolin for 1.5 hours to induce the expression of both Pck1 and G6pc genes, which mimics the fasting and PGC-1α-mediated gluconeogenic response. The dose response curves were used to calculate an inhibitory activity of the compounds by determining the difference in Ct values between compound treatment and forskolin control at each dose, and provided an estimated potency of the compounds in suppressing Pck1 and G6pc (FIGS. 4, 34). As a result, 42 compounds were selected with an estimated inhibitory AC50 of <10 µM for either Pck1 or G6pc. These compounds are inhibitors of forskolin-induced gluconeogenic gene expression and predicted to reduce glucose production. To specifically test the inhibitory activity of the remaining small molecule positive hits on PGC-1α-mediated glucose production, adenoviruses to ectopically express PGC-1α in primary hepatocytes were used. Similar to forskolin, PGC-1α overexpression induces gluconeogenic gene expression and promotes glucose release. Primary hepatocytes were treated with the chosen positive hit compounds that could suppress gluconeogenic gene expression, and the concentration of glucose released to the culture medium was measured. In this small assay screen, 9 compounds significantly suppressed glucose release compared to control (FIG. 5 and Tables 1 and 2). Interestingly, metformin is only able to suppress glucose production at a higher concentration (100-250 µM), compared to the identified compound collection (20 µM), highlighting the potency of these chemical scaffolds to inhibit glucose output. Taken together, using a high-throughput chemical screen platform, chemical scaffolds have been identified that induce acetylation of PGC-1α, suppress expression of gluconeogenic genes and reduce glucose production. Due to their ability to inhibit glucose release from hepatocytes, these compounds can potentially be used as anti-diabetic drugs (e.g., to reduce blood glucose through suppression of HGP). These scaffolds provide chemical tools that can be used, not only to develop new anti-diabetic drugs, but also to identify molecular and metabolic pathways that regulate HGP.

Example 4—SR-18292 Suppresses Hepatic Gluconeogenic Gene Expression and Glucose Production in Primary Hepatocytes To test anti-diabetic effects of the positive hits that scored in all the assays described above, the most potent compounds were selected that decreased glucose production. Compound 82 (C-82) was the top small molecule hit suppressing glucose production (FIG. 5). However, C-82 showed poor bioavailability and solubility (data not shown) and would require extensive structure-activity relationship (SAR) studies to test this compound in vivo. Therefore, the next most potent small molecule, compound 80 (C-80), was selected for further validation and characterization. C-80 is part of the NIH Molecular Libraries Compound Collection and has been screened against 545 bioassays that represent diverse targets and a range of readouts. C-80 was found active in only 14 bioassays (2.5%), two of these bioassays are part of our high-throughput screens, highlighting the lack of promiscuity of C-80. Moreover, C-80 showed the highest potency in a confirmatory screen.

Figure 6:
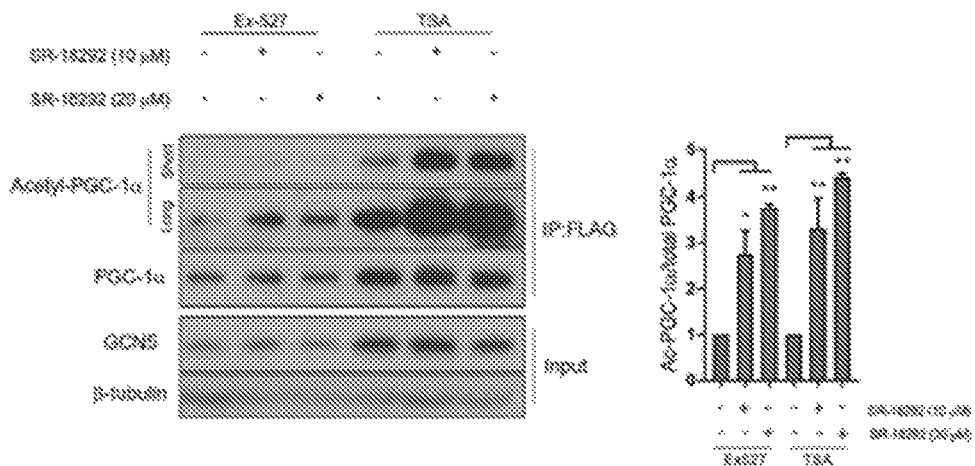
FIG. 6 depicts data showing the western blot analysis of PGC-1α acetylation following treatment with SR-18292 in the presence of the SIRT1 inhibitor, Ex527 (5 mM) and the pan HDACs inhibitor TSA (1 mM). Hepatocytes were infected with Ad-PGC-1α and Ad-GCN5 and treated with SR-18292 for 18 h. IP, immunoprecipitation.

Due to limited commercial availability, an analog of C-80 was synthesized, SR-18292. This analog is identical to C-80, except the methyl group on the 3' position on the indole group that is lacking in SR-18292. To confirm that the effects of SR-18292 were similar to C-80, primary hepatocytes were treated with SR-18292, which increased PGC-1α acetylation (FIG. 6). The acetylation status of PGC-1α is determined by its dynamic interaction with deacetylases and acetyl transferases, primarily SIRT1 and GCN5. Interestingly, SR-18292 increased acetylation of PGC-1α even in the presence of Ex-527, a selective SIRT1 inhibitor, and Trichostatin A (TSA), a pan-histone deacetylase (HDAC) inhibitor. This result suggests that the increased acetylation of PGC-1α, induced by SR-18292, is mediated by a mechanism that does not involve inhibition of either SIRT1 or other HDACs.

Figure 7:
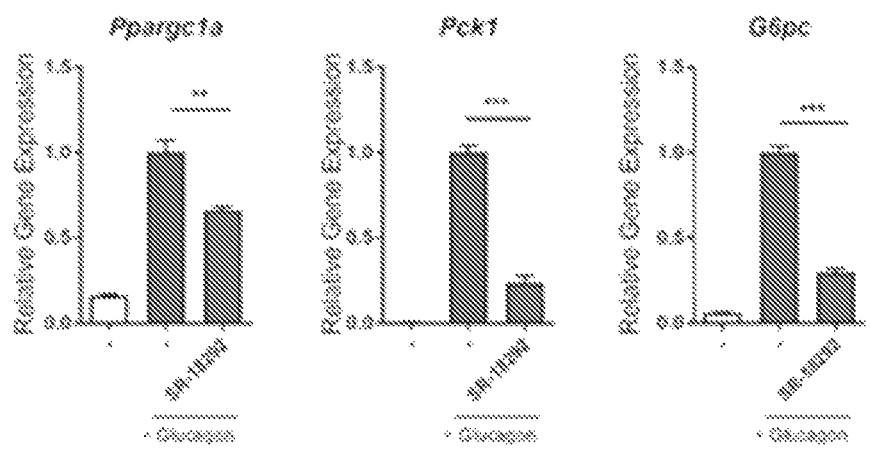
FIG. 7 and FIG. 8 show the qPCR analysis of Ppargc1a, Pck1 and G6pc mRNA expression levels following treatment with SR-18292 (20 mM) in isolated primary hepatocytes.
Figure 35:
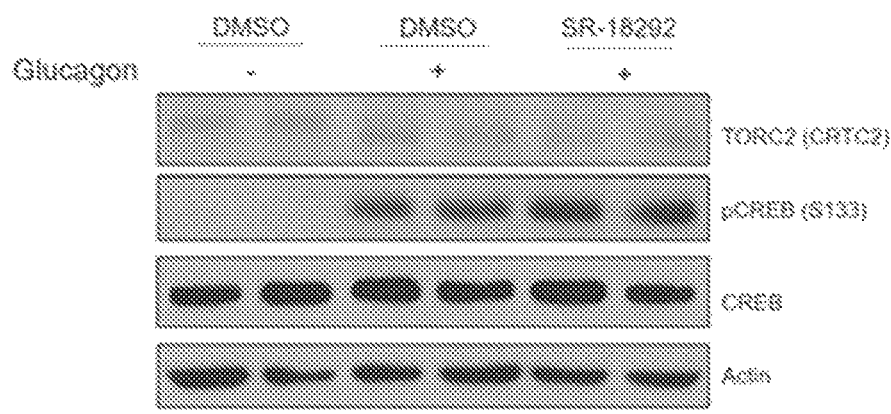
FIG. 35 depicts the Western blot analysis of CREB phosphorylation (S133) and total TORC2 upon glucagon stimulation (200 nM) and SR-18292 treatment (20 mM). Glucagon-stimulated dephosphorylation of TORC2 results in a shift in gel band.
Figure 36:
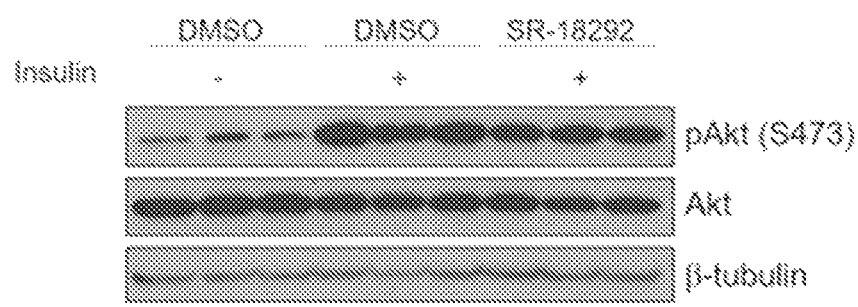
FIG. 36 depicts the Western blot analysis of Akt phosphorylation (S473) upon insulin stimulation (100 nM) and SR-18292 treatment (20 mM).
Figure 37:
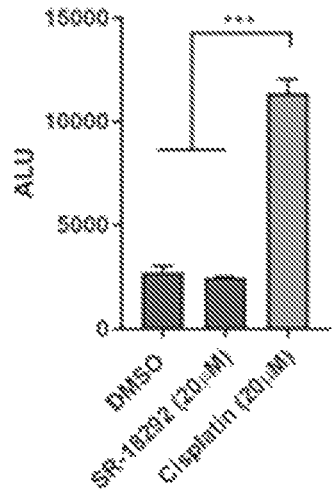
FIG. 37 depicts data assessing cellular viability using the Toxilight bioassay kit (Lonza) (n=3). Culture medium was collected from hepatocytes treated with either SR-18292 or cisplatin for 18 hrs. ***$P<0.001$.
Figure 38:
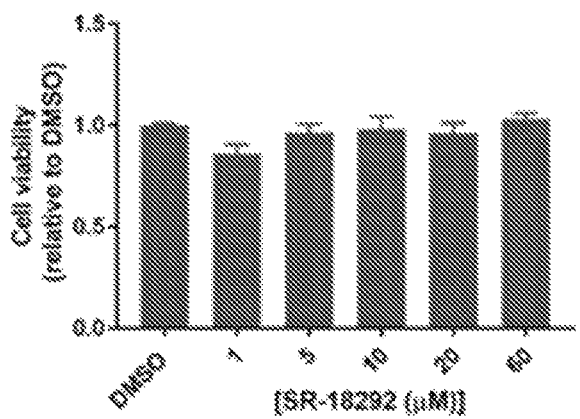
FIG. 38 depicts data assessing cellular viability using the MTT assay (n=4).
Figure 39:
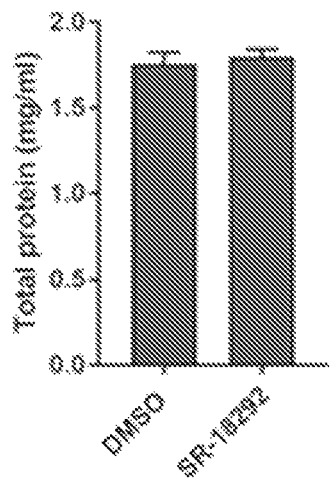
FIG. 39 is a bar graph showing Total protein levels are not affected by SR-18292 treatment. n=3.

Upon fasting, increased plasma glucagon levels induce gluconeogenic genes in the liver, and PGC-1α is a component of this response. In agreement with SR-18292 inhibiting PGC-1α gluconeogenic function, treatment of hepatocytes with SR-18292 significantly reduced the ability of glucagon to stimulate Pck1 and G6pc gene expression (FIG. 7). This was achieved without disrupting the canonical glucagon-induced increases in phosphorylation of CREB and dephosphorylation of CRTC2 (FIG. 35). In addition, cell autonomous enhancement of insulin signaling was not observed (FIG. 36), suggesting that the effect of SR-18292 on gene expression at the cellular level is probably downstream of the signaling cascade that results in activation of CREB and Akt. Importantly, SR-18292 did not cause hepatocyte toxicity as measured by cell viability or total protein levels (FIGS. 37-39).

Figure 8:
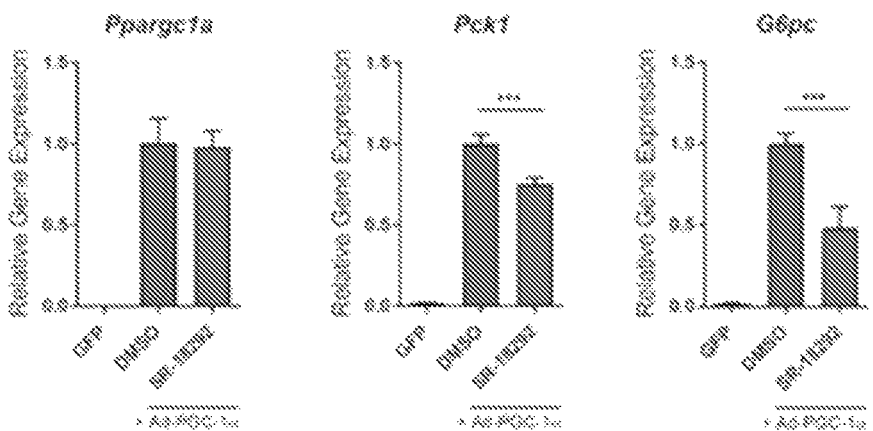
Figure 9:
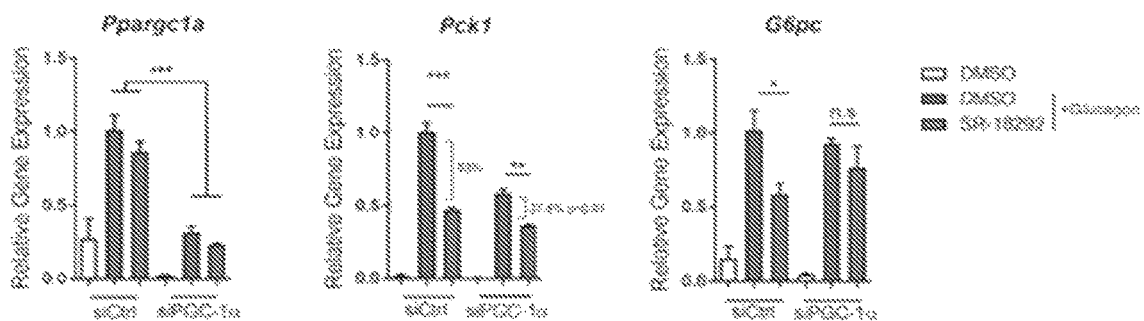
FIG. 9 shows the qPCR analysis of Ppargc1a, Pck1 and G6pc mRNA expression levels following SR-18292 (20 mM) treatment and siRNA to reduce to expression of Ppargc1a. Difference in % repression of Pck1 was calculated using two-way ANOVA with Sidak posttest.
Figure 10:
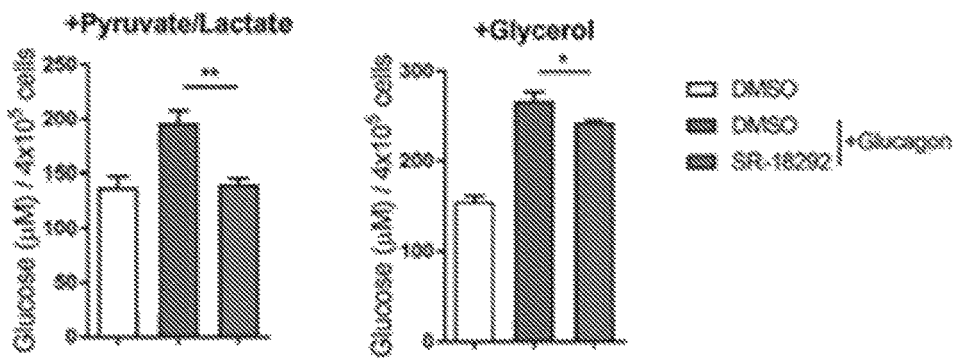
FIG. 10 and FIG. 11 show data representing glucose production by primary hepatocytes following treatment with SR-18292 (20 mM). Hepatocytes were treated with either glucagon (200 nM) or infected with Ad-PGC-1α to induce glucose production. All data from FIGS. 6-11 presented as mean+/−S.E.M. n=3, one-way ANOVA with Tuckey posttest. Representative of at least 2 independent experiments. *$P<0.05$, $P<0.01$, *$P<0.001$. n.s=not significant.
Figure 11:
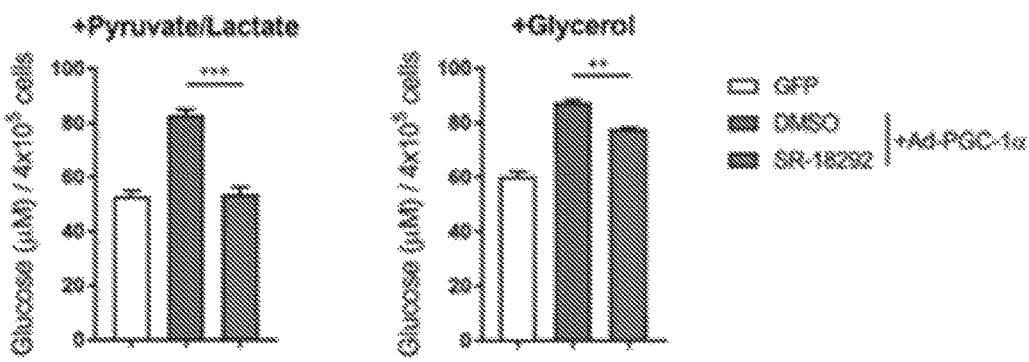
Figure 40:
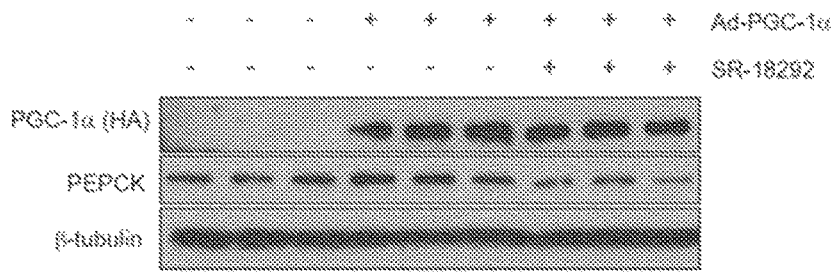
FIG. 40 depicts data showing PEPCK protein levels are reduced in hepatocytes treated with SR-18292 and infected with Ad-PGC-1α.
Figure 41:
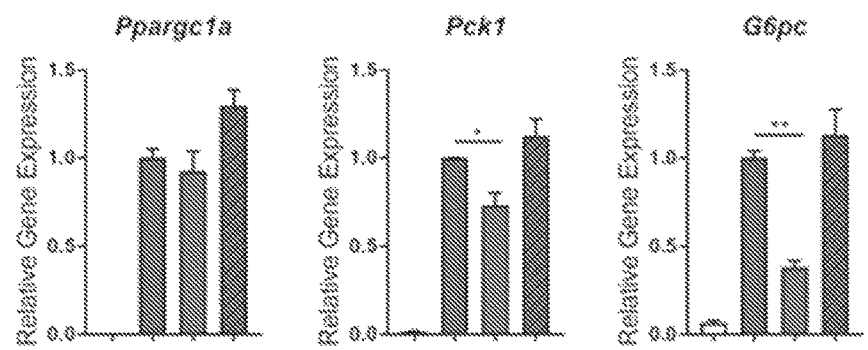
FIG. 41 depicts data showing mRNA expression level of Ppargc1a, Pck1 and G6pc following 18 h treatment with the SR-18292 (20 mM).
Figure 42:
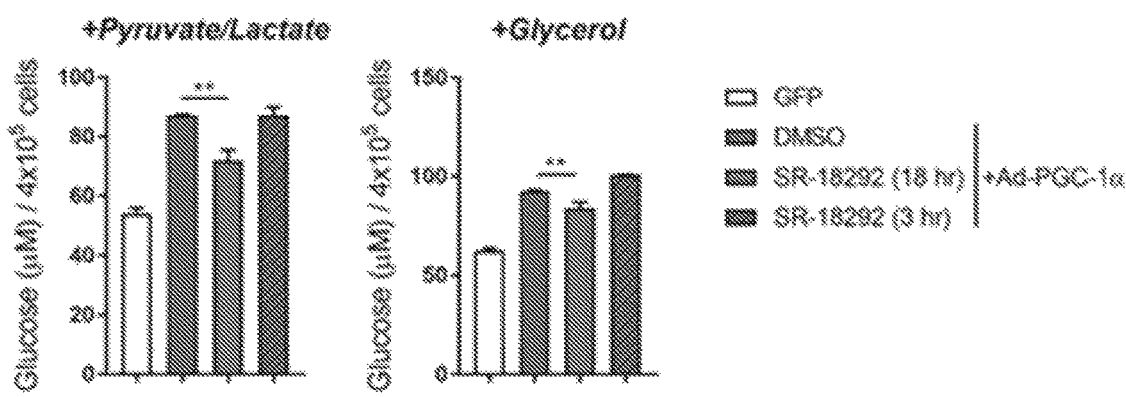
FIG. 42 depicts data showing glucose release from either Pyruvate/lactate (2 mM/20 mM) or glycerol (10 mM) when hepatocytes were infected with Ad-PGC-1α.

As a major regulator of Pck1 and G6pc transcription, overexpression of PGC-1α in hepatocytes is sufficient to induce expression of these genes. Similar to its effects with glucagon, SR-18292 significantly reduced gluconeogenic gene and protein expression induced by ectopic expression of PGC-1α (FIGS. 8 and 40). Since increased gluconeogenic gene expression is driven solely by PGC-1α in these experiments, the suppression of these genes suggests a direct effect of SR-18292 on the PGC-1α transcriptional complex that inhibits expression of Pck1 and G6pc genes. Reducing the expression of PGC-1α by siRNA significantly impairs the ability of SR-18292 to suppress Pck1 and G6pc, suggesting that its effect is at least partially mediated by PGC-1α (FIG. 9). Consistent with the effects on suppression of gluconeogenic genes, SR-18292 significantly reduced glucagon- and PGC-1α-mediated glucose production in isolated hepatocytes (FIGS. 10 and 11). Interestingly, SR-18292 decreases glucose production when pyruvate and lactate are used as substrates for gluconeogenesis as well as when glycerol is used as a substrate (FIGS. 10 and 11). The reduction in glucose production correlated with suppression of Pck1 and G6pc since short treatment with SR-18292 (3 hr) had no effect on gene expression or glucose release (FIGS. 41 and 42). Together, these results show that SR-18292 is a potent inhibitor of the gluconeogenic gene expression and glucose production in hepatocytes.

Example 5—SR-18292 Increases the Interaction of PGC-1α with GCN5 and Reduces Co-Activation of HNF4α by PGC-1α

Figure 12:
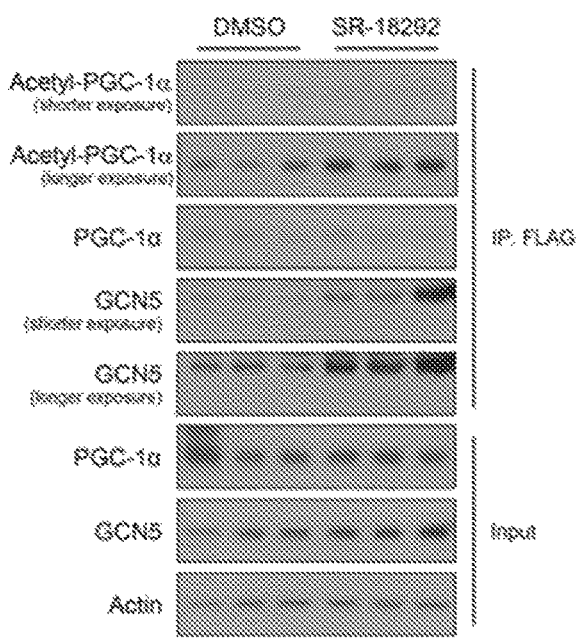
FIG. 12 is an image of a blot showing the co-immunoprecipitation (Co-IP) of FLAG-PGC-1α following treatment with SR-18292 (10 mM).
Figure 43:
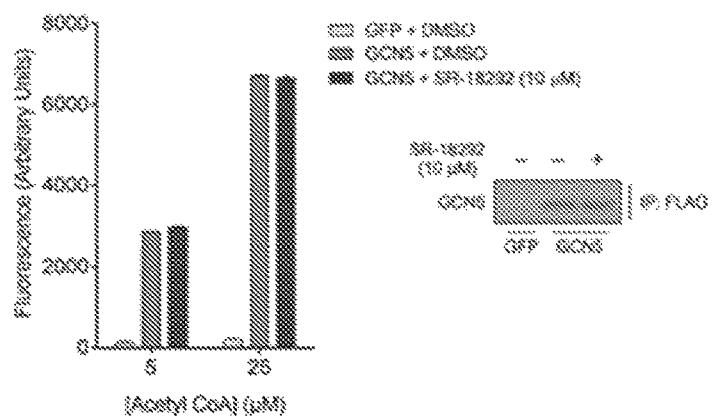
FIG. 43 depicts HAT activity assay data showing that the acetyl transferase activity of GCN5 toward H3 peptide is not increased in cells treated with SR-18292. n=3.
Figure 44:
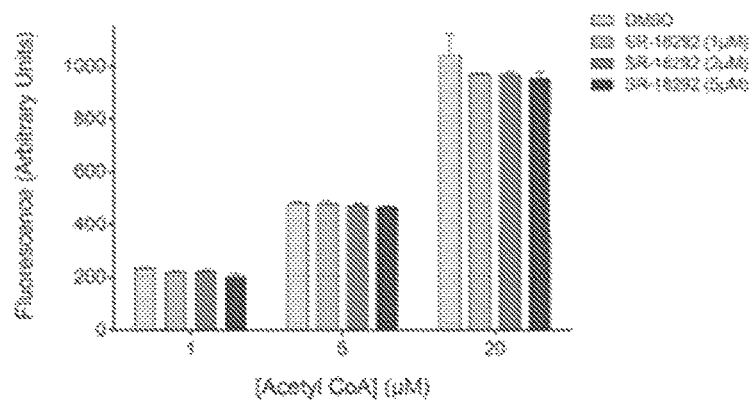
FIG. 44 depicts HAT activity assay data showing that the acetyl transferase activity of GCN5 toward H3 peptide is not affected by in-vitro treatment with SR-18292. n=3.
Figure 45:
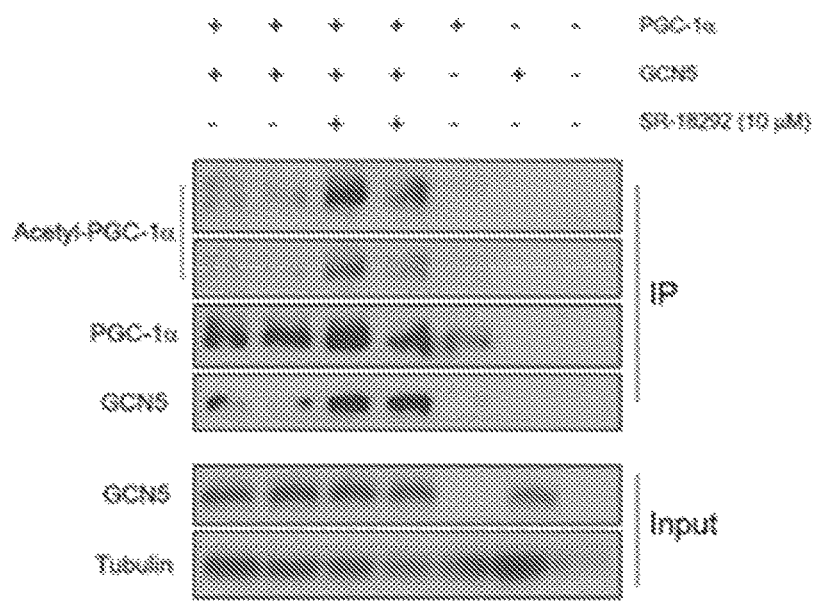
FIG. 45 is an image of a blot showing the interaction of PGC-1α with ectopically expressed GCN5 is increased after treatment with SR-18292.
Figure 46:
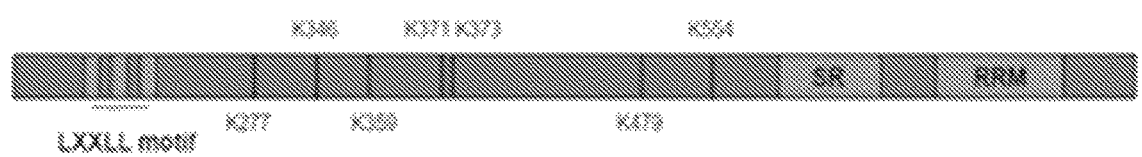
FIG. 46 identifies the lysine residues whose acetylation is increased when U-2 OS cells were infected with Ad-PGC-1α and Ad-GCN5 and treated with SR-18292 (10 mM) for 18 h.

The PGC-1α acetylation data from primary hepatocytes (FIG. 6) implies that SR-18292 induces acetylation by a mechanism that does not involve inhibition of HDACs. The possibility that the SR-18292-mediated increase in PGC-1α acetylation is modulated by GCN5, an acetyl transferase known to acetylate PGC-1α, was tested. First, whether the catalytic activity of GCN5 is increased as a result of SR-18292 treatment was tested. To this end, GCN5 was overexpressed and subsequently immunoprecipitated (IP) from U-2 OS cells treated with SR-18292. It was found that the catalytic activity was not changed compared to GCN5 IPed from control cells (FIG. 43). In addition, SR-18292 does not directly activate GCN5 since in vitro treatment of IPed GCN5 did not result in increased activity (FIG. 44). It was then speculated that while the catalytic activity of GCN5 is not changed by SR-18292, its physical interaction with PGC-1α might be modulated by this treatment. Ectopic expression and co-IP of PGC-1α from U-2 OS cells revealed that the interaction of endogenous GCN5, as well as ectopically expressed GCN5, with PGC-1α was increased in cells that were treated with SR-18292 (FIGS. 12 and 45). To identify the PGC-1α lysine residues that are affected by treatment with SR-18292, mass spectrometry analysis was performed and identified 7 lysine residues whose acetylation was increased (FIG. 46). Two of these sites (K277 and K346) were previously described, and the increased acetylation of these sites is associated with reduced gluconeogenic activity of PGC-1α. Together, these results suggest that by increasing the interaction of GCN5 with PGC-1α, SR-18292 increases the acetylation of specific PGC-1α lysine residues that might subsequently decrease its gluconeogenic activity.

Figure 13:
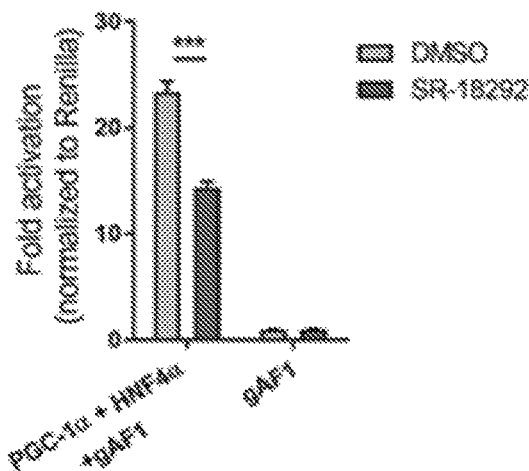
FIG. 13 is a bar graph showing data when U-2 OS cells were transfected with the indicated plasmids and luciferase reporter levels were measured after 24 hours. n=3, two-way ANOVA with Sidak posttest. Representative of at least 2 independent experiments. *$P<0.05$, $P<0.01$, *$P<0.001$.
Figure 14:
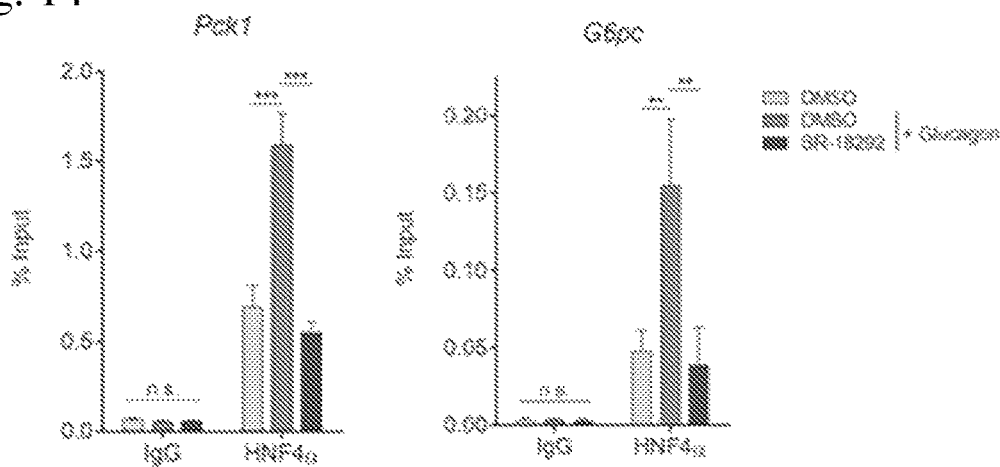
FIG. 14 depicts data showing the Pck1 and G6pc promoters' occupancy by HNF4a was determined following chromatin IP (ChIP) using HNF4a specific antibody. Glucagon (200 nM) was used to promote HNF4a binding to these promoter regions. n=3, one-way ANOVA with Tuckey posttest. Representative of at least 2 independent experiments. *$P<0.05$, $P<0.01$, *$P<0.001$.
Figure 15:
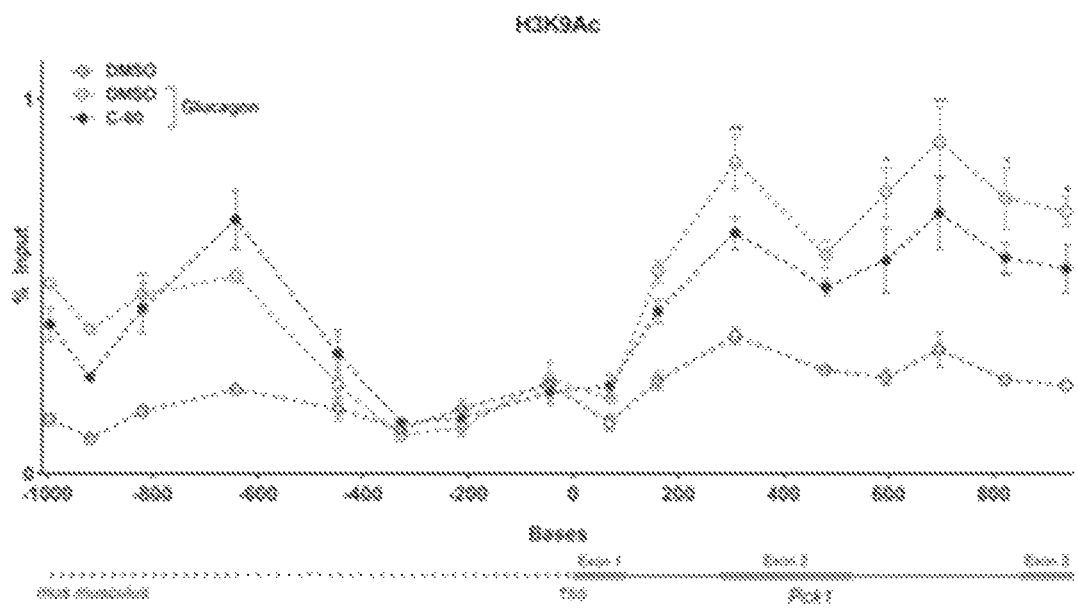
FIG. 15 and FIG. 16 depict data showing H3K9Ac and H3K4me3 marks on Pck1 gene are reduced upon treatment. n=3, two-way ANOVA with Tuckey posttest.
Figure 16:
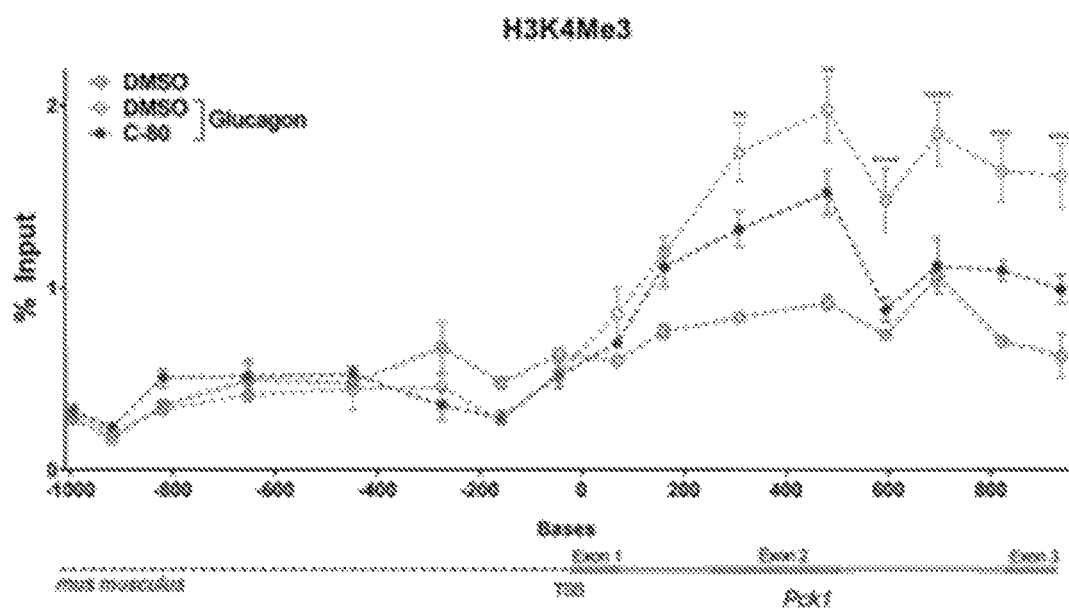
Figure 47:
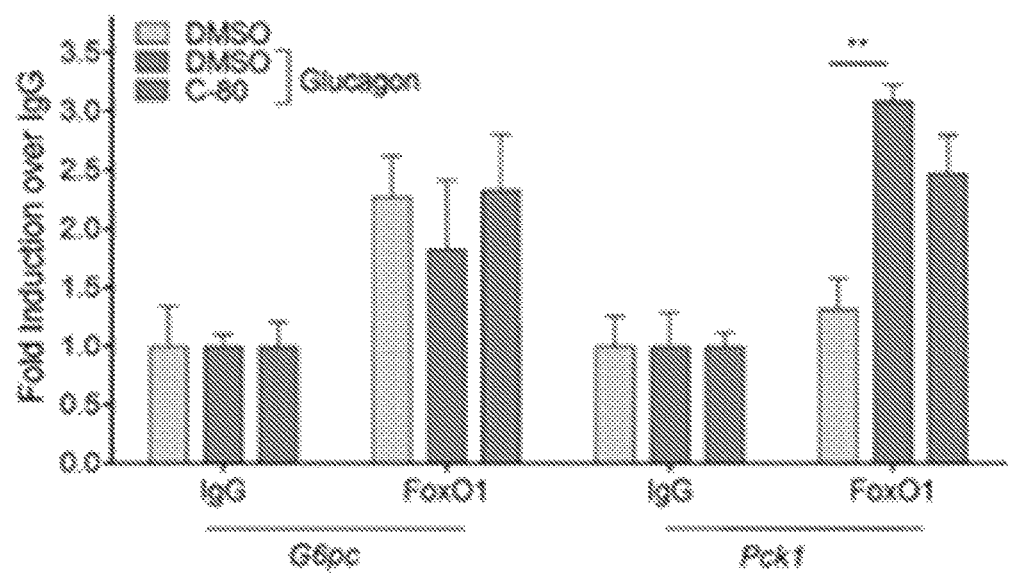
FIG. 47 is a bar graph showing that Promoter occupancy of FoxO1 over Pck1 and G6pc promoter regions is not affected by drug treatment. n=3. **, P<0.01.

The GCN5 acetyl transferase complex decreases PGC-1α gluconeogenic transcriptional activation by interacting with PGC-1α. This is achieved at least in part by reducing the ability of PGC-1α to co-activate the nuclear hormone receptor HNF4α. Co-activation of HNF4α by PGC-1α is required to promote transcription of the gluconeogenic genes Pck1 and G6pc. To test whether SR-18292 reduces the transcriptional activity of HNF4α that is induced by PGC-1α, a luciferase reporter construct driven by a fragment of the Pck1 promoter containing an HNF4α binding site was used. In agreement with the enhanced interaction between PGC-1α and GCN5, the transcriptional activity of HNF4α was significantly reduced in cells treated with SR-18292 (FIG. 13). To further characterize the SR-18292-mediated inhibition of HNF4α transcriptional activity, chromatin immunoprecipitation (ChIP) assays were performed to examine the promoter occupancy of HNF4α on Pck1 and G6pc promoters. Primary hepatocytes were treated with glucagon to induce gluconeogenic gene transcripts, and antibodies against HNF4α were used to IP chromatin fragments bound to this protein. In accordance with the inhibitory effect of SR-18292 on Pck1 and G6pc expression, the glucagon-induced Pck1 and G6pc promoter occupancy by HNF4α was significantly reduced in cells treated with SR-18292 (FIG. 14). The FoxO1 promoter occupancy was not altered (FIG. 47), suggesting that this effect is specific to HNF4α. Epigenetic changes accompany the response to glucagon in the fasted state, including an increase in activating H3K9 acetylation (H3K9Ac) and H3K4 trimethylation (H3K4Me3) of the Pck1 and G6pc genes. Interestingly, compound-treated hepatocytes had reduced H3K9Ac and H3K4Me3 marks on the Pck1 gene (FIGS. 15 and 16), further supporting the findings that upon treatment, transcription of this gene is less active. These results suggest that by modulating the interaction between GCN5 and PGC-1α, SR-18292 inhibits the gluconeogenic activity of PGC-1α and reduces co-activation of HNF4α. In addition, SR-18292 treatment decreases occupancy of HNF4α on Pck1 and G6pc promoters, leading to reduced expression of gluconeogenic genes.

TABLE 4

Primers used for detection of H3K9Ac/H3K4Me3 abundance on Pck1 gene

| Primer | Amplicon Midpoint | Forward Primer (5'-3') | Reverse Primer (5'-3') |
|---|---|---|---|
| 1 | −995 | AATTGGCATGAAGGTCTGTG | CTTGAATGCCCAAGTGTCTG |
| 2 | −919 | CAGACACTTGGGCATTCAAG | CTGCGTTAGACACCATCACC |
| 3 | −819 | GGTGATGGTGTCTAACGCAG | AGACCAGGAAACTGAGGCAG |
| 4 (H3K4Me3) | −652 | CTGCCTCAGTTTCCTGGTCT | CCATCCCAAGATGAACACTG |
| 4 (H3K9Ac) | −642 | CTGCCTCAGTTTCCTGGTCT | GTGTGTGGTGGATTCTCTGG |
| 5 | −448 | CAGTGTTCATCTTGGGATGG | AGACGCCTCTTGGACTTCAT |
| 6 (H3K4Me3) | −274 | ATGAAGTCCAAGAGGCGTCT | TAATGAATGTTGGGAGGCCT |
| 6 (H3K9Ac) | −328 | ATGAAGTCCAAGAGGCGTCT | GGCTCTTGCCTTAATTGTCAG |
| 7 (H3K4Me3) | −158 | AGGCCTCCCAACATTCATTA | ATCATAGCCATGGTCAGCAC |
| 7 (H3K9Ac) | −212 | CTGACAATTAAGGCAAGAGCC | ATCATAGCCATGGTCAGCAC |
| 8 | −45 | GTGCTGACCATGGCTATGAT | GTTGACCGAGGGTGTGTTC |
| 9 | 69 | GAACACACCCTCGGTCAAC | ATGAAATGACCCTGCCTACC |
| 10 | 161 | GGTAGGCAGGGTCATTTCAT | TCTCGGTCCTTCCGTAGACT |
| 11 | 308 | AGTCTACGGAAGGACCGAGA | TTCCACGAACTTCCTCACTG |
| 12 | 480 | CAGTGAGGAAGTTCGTGGAA | CCAGAGAGTTAGGGCTGAGG |
| 13 | 594 | CCTCAGCCCTAACTCTCTGG | TTCTCAGGTGTTTGCTACGG |

TABLE 4-continued

Primers used for detection of H3K9Ac/H3K4Me3 abundance on Pck1 gene

| Primer | Amplicon Midpoint | Forward Primer (5'-3') | Reverse Primer (5'-3') |
|---|---|---|---|
| 14 | 696 | CCGTAGCAAACACCTGAGAA | CAAGGACAACAGGAGCTTGA |
| 15 | 822 | TCAAGCTCCTGTTGTCCTTG | CATCTCGAGGGTCAGTGAGA |
| 16 | 937 | TCTCACTGACCCTCGAGATG | AGTCCTCTTCCGACATCCAG |

TABLE 5

Primers used for detection of HNF4α/FoxO1 Pck1 and G6pc promoters' occupancy

| Gene | Forward Primer (5'-3') | Reverse Primer (5'-3') |
|---|---|---|
| G6pc | CACCCTGAACATGTTTGCAT | GGCCTTGATCCCTCTGCTAT |
| Pck1 | ATGAAGTCCAAGAGGCGTCT | GGCTCTTGCCTTAATTGTCAG |

Figure 48:
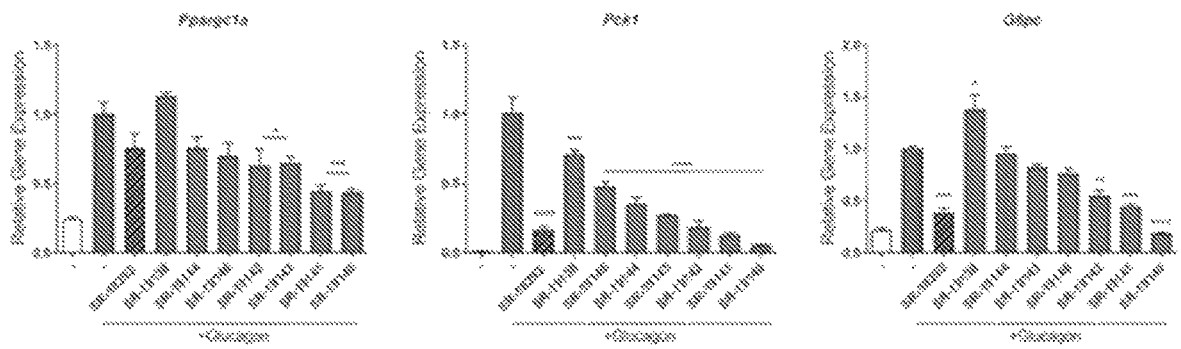
FIG. 48 depicts data showing the mRNA expression level of Ppargc1a, Pck1 and G6pc following 18 h treatment with the indicated compounds (20 mM). Glucagon stimulation (200 nM) was used to induce the expression of Pck1 and G6pc genes.
Figure 49:
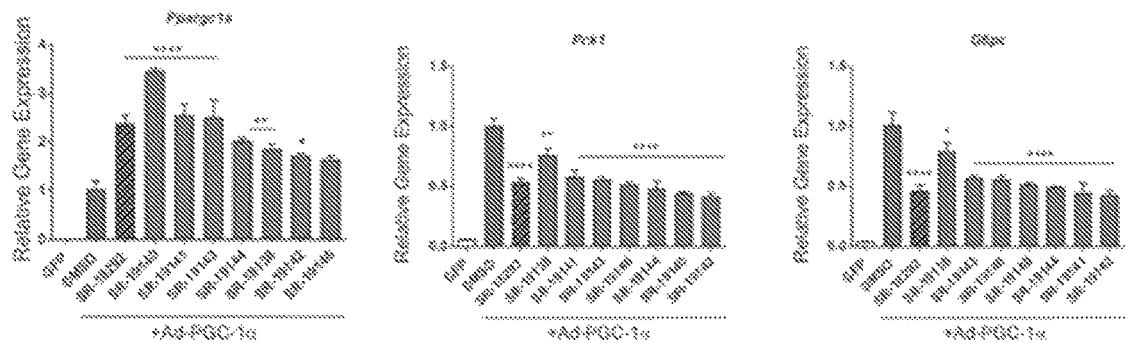
FIG. 49 depicts data showing the mRNA expression level of Ppargc1a, Pck1 and G6pc following 18 h treatment with the indicated compounds (20 mM). Hepatocytes were infected with Ad-PGC-1α to induce expression of Pck1 and G6pc genes.
Figure 50:
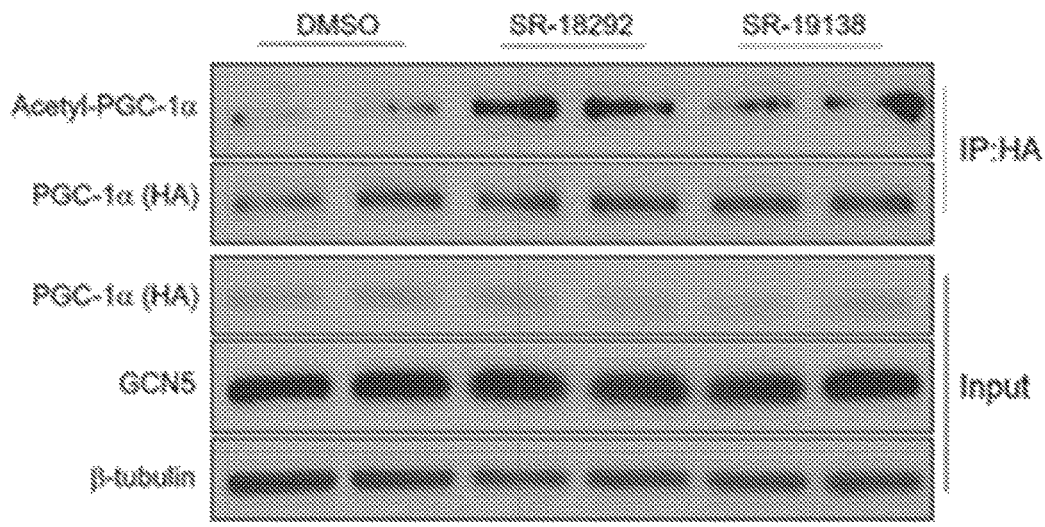
FIG. 50 shows the use of Western blot analysis to detect acetylation status of PGC-1α following treatment with SR-18292 (10 mM) and SR-19138 (10 mM). U-2 OS cells were infected with Ad-PGC-1α and Ad-GCN5 and treated with the indicated compound for 18 h. PGC-1α was immunoprecipitated using FLAG beads.

Example 6—Identification of SR-18292 Small Molecule Analogs Lacking Gluconeogenic Inhibitory Effects To gain further insights into the mode of action of SR-18292, SAR studies were performed to search for chemical modifications that impair its activity, as this might reveal the active site of the compound. A panel of chemical analogs were generated and were tested for their ability to suppress gluconeogenic gene expression induced by either glucagon or PGC-1α overexpression. Interestingly, the replacement of the indole group with phenyl (Table 1, SR-19138) reduced the inhibitory effect of the new scaffold on glucagon or PGC-1α-increased Pck1 and G6pc expression (FIGS. 48 and 49). Other analogs of the compound had little or no effect on gluconeogenic activity (FIGS. 48 and 49). This suggests that hydrogen bond interaction in this part of the molecule might be important for activity. The reduced effect of the new analog on suppression of Pck1 and G6pc correlated with a reduced ability to induce acetylation of PGC-1α compared to the parent compound, SR-18292 (FIG. 50). These results indicate that the indole group is involved in the bioactivity of SR-18292.

Figure 17:
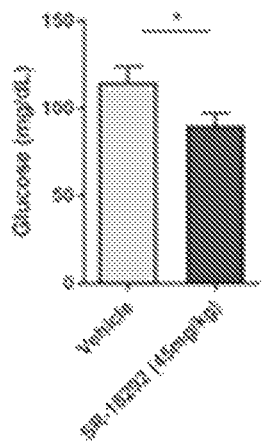
FIG. 17 is a bar graph depicting data representing fasting blood glucose levels of mice fed HFD for 13 weeks. n=10, two-tailed student's t-test.
Figure 18:
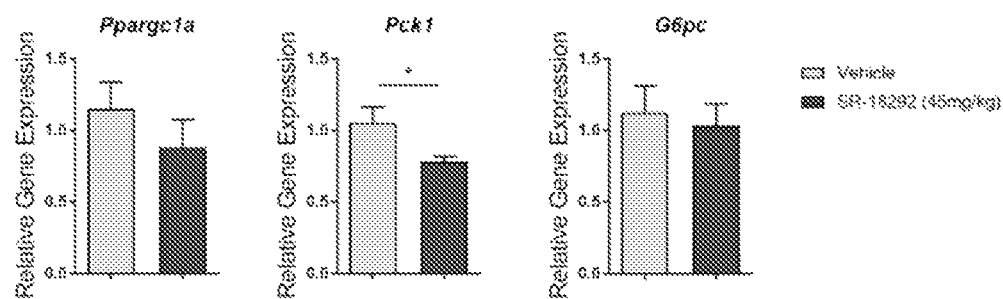
FIG. 18 is a bar graph depicting data representing qPCR analysis of Ppargc1a, Pck1 and G6pc from liver tissue isolated from fasted mice treated with SR-18292. n=10, two-tailed student's t-test.

Example 7—SR-18292 Reduces Fasting Blood Glucose, Increases Hepatic Insulin Sensitivity and Improves Glucose Homeostasis in Diabetic Mice Based on the potent gluconeogenic suppressor effects of SR-18292 in primary hepatocytes, its potential use as an anti-diabetic drug was tested. In the fasted state, the liver contributes to regulating blood glucose levels through the release of glucose into the circulation. Therefore, blood glucose was measured in the fasted state during which the liver plays a major role maintaining glycemia. Preliminary pharmacokinetics (PK) studies with the original C-80 revealed that the compound concentration in the liver, 2 h following a single dose (30 mg/kg) administration via intraperitoneal (I.P.) injection, was 2.3 μM. It was projected that multiple injections of a higher dose might be sufficient to reach active concentration in the liver. A high fat diet (HFD) fed mice, a dietary model of obesity and T2D, were used. Mice were treated with SR-18292 (45 mg/kg) via I.P. injection for 3 consecutive days and again on day 4 before measuring fasting blood glucose. Strikingly, mice that were treated with SR-18292 had significantly lower levels of fasting blood glucose concentrations compared to matched vehicle-treated control mice (FIG. 17). The induction of gluconeogenic gene expression is a regulatory component of the response to fasting. Importantly, gluconeogenic gene expression, specifically that of Pck1, is inhibited in livers isolated from mice treated with SR-18292 (FIG. 18), suggesting that SR-18292 targets similar hepatic glucose metabolic pathways both in vitro and in vivo.

Figure 19:
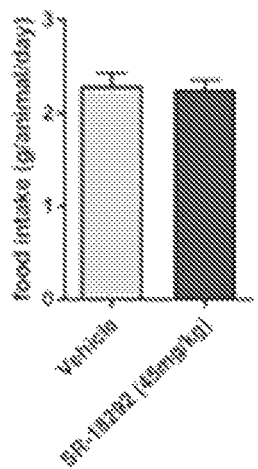
FIG. 19 is a bar graph depicting data representing food intake measured during the first 48 hours of treatment with SR-18292. Pulled data from 4 different experiments is presented. In each, experiment n=7-9.
Figure 20:
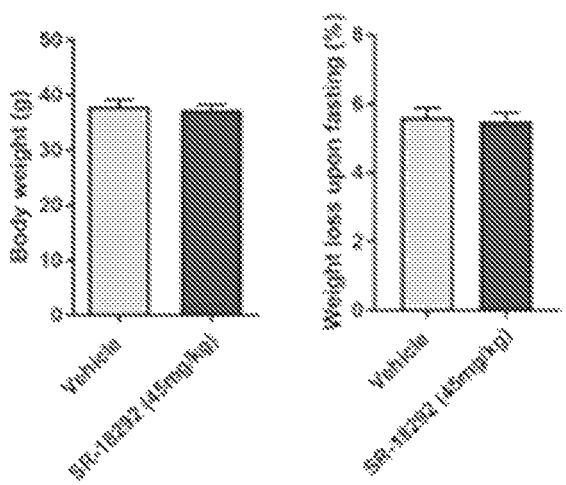
FIG. 20 is a bar graph depicting data representing body weight of mice following treatment with SR-18292. n=10. Weight loss data upon overnight fasting is pulled from 3 different experiments.
Figure 21:
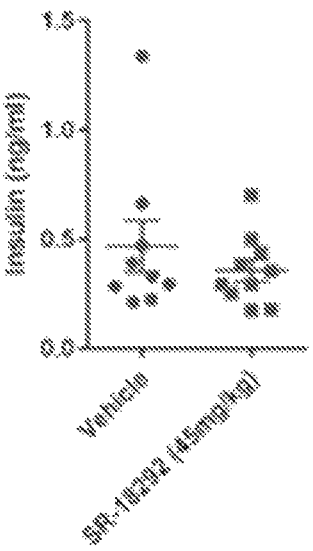
FIG. 21 is a plot showing fasting insulin levels of mice fed HFD for 13 weeks and treated with SR-18292.
Figure 22:
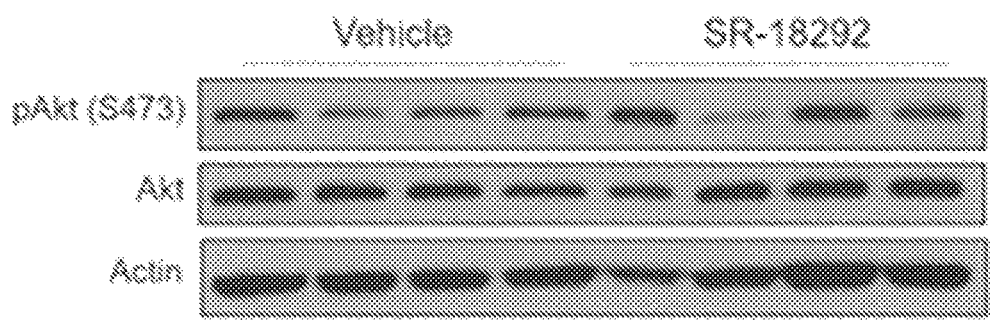
FIG. 22 shows the Western blot analysis of pAkt levels in liver tissues from fasted mice treated with SR-18292.
Figure 23:
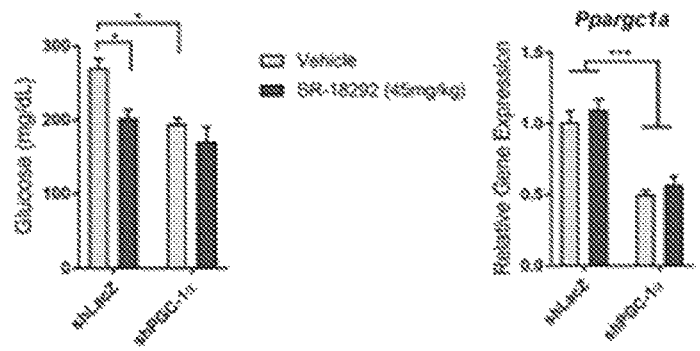
FIG. 23 is a bar graph depicting data representing blood glucose levels of after $Lep^{ob/ob}$ mice were administered adenoviruses expressing shLacZ or shPGC-1α via tail vein injection. Blood glucose was measured on day 8 post infection. Livers were collected to verify knockdown efficiency. *$P<0.05$, $P<0.01$, *$P<0.001$.
Figure 24:
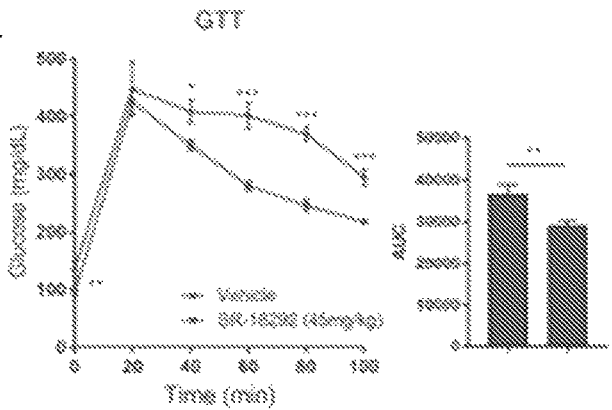
FIG. 24 is a plot showing GTT in mice fed HFD for 14 weeks. n=7/vehicle, n=8/SR-18292, Two-way ANOVA with Sidak posttest. *$P<0.05$, $P<0.01$, *$P<0.001$. AUC, area under the curve.
Figure 25:
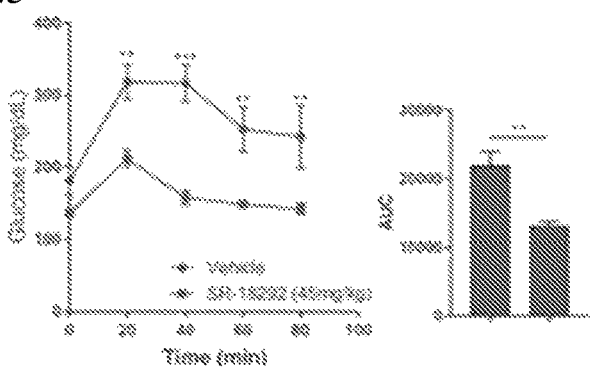
FIG. 25 is a plot showing GTT in $Lep^{ob/ob}$ mice. 9 weeks old mice were used. n=6, Two-way ANOVA with Sidak posttest. *$P<0.05$, $P<0.01$, *$P<0.001$. AUC, area under the curve.
Figure 26:
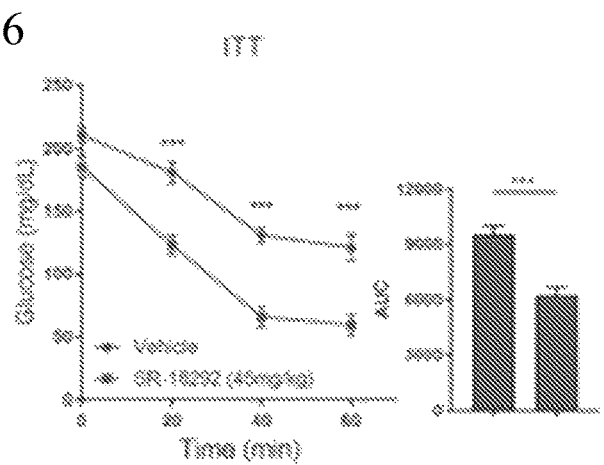
FIG. 26 is a plot showing ITT in mice fed HFD for 3 weeks. n=6, Two-way ANOVA with Sidak posttest. *$P<0.05$, $P<0.01$, *$P<0.001$. AUC, area under the curve.
Figure 51:
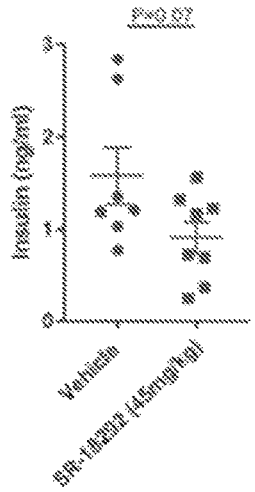
FIG. 51 is a plot showing the plasma insulin levels after GTT.
Figure 57:
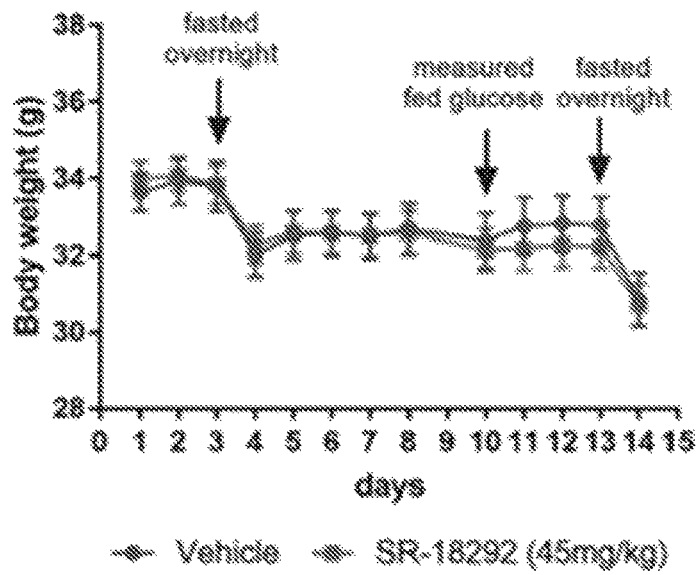
FIG. 57 is a plot monitoring body weight over a period of days. Mice fed HFD for 6 weeks were injected daily with SR-18292 for a total of 14 days and body weight was monitored during the treatment.
Figure 58:
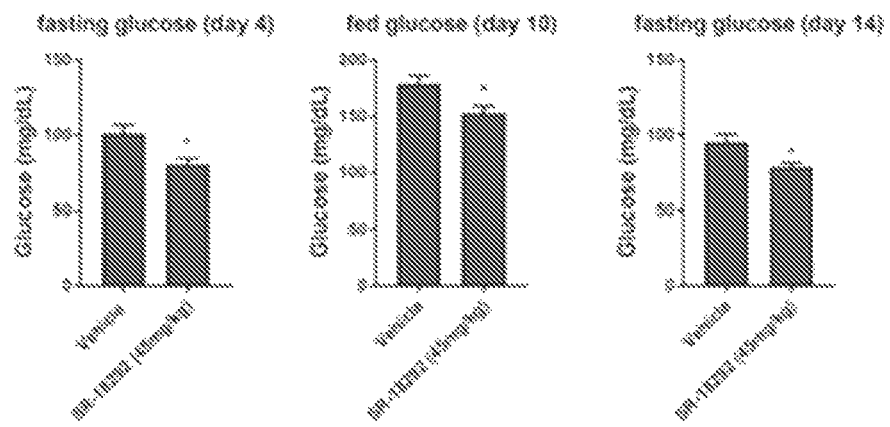
FIG. 58 is a series of bar graphs monitoring blood glucose. Mice were fasted at day 3 and 13 and fasting blood glucose was measured at day 4 and 14. Fed blood glucose was also measured at day 10. n=10, *P<0.05.
Figure 59:
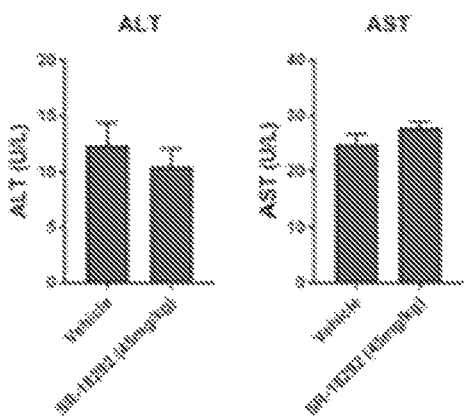
FIG. 59 depicts two bar graphs showing that Serum ALT and AST levels were not altered after 14 days of SR-18292 treatment. n=10.
Figure 60:
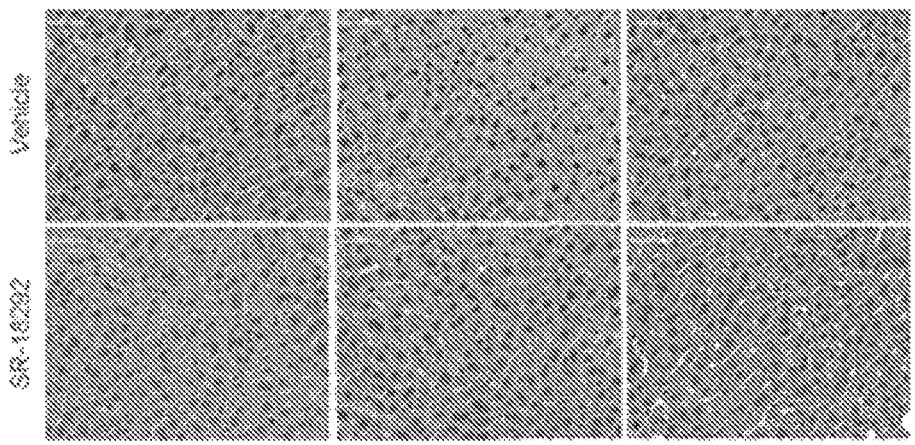
FIG. 60 is an image of H&E staining of liver slices obtained from livers harvested after 14 days of SR-18292 treatment. 3 representative images are presented for each group. All samples (n=10/vehicle, n=10/SR-18292) were assessed by an expert mouse pathologist and no sign of toxicity was observed. scale bar, 50 mm.
Figure 61:
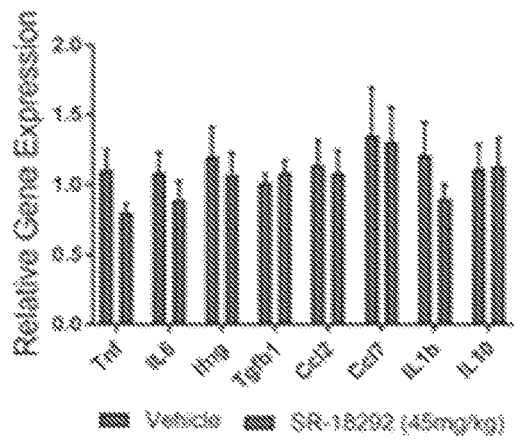
FIG. 61 is bar graph showing expression level of inflammatory genes from livers harvested after 14 days of SR-18292 treatment. n=10.

The reduction in fasting blood glucose concentration is not likely to be a result of reduced calorie consumption as neither food intake nor body weight were changed as a result of treatment with SR-18292 (FIGS. 19 and 20). In addition, liver toxicity, as measured by serum levels of alanine transaminase (ALT), aspartate aminotransferase (AST), lactate dehydrogenase (LDH) and bilirubin, was not observed in mice treated with SR-18292 (Table 6). Basal blood insulin levels, while trending lower, were not significantly changed as a consequence of SR-18292 treatment as indicated by similar fasting blood insulin levels in both the SR-18292-treated and the vehicle control groups (FIG. 21). In addition, phosphorylation of Akt was also not changed (FIG. 22), suggesting that SR-18292 does not exert its blood glucose-lowering effects by affecting insulin secretion or canonical insulin signaling. To assess the contribution of PGC-1α in mediating the in vivo effects of SR-18292, hepatic PGC-1α in Lep$^{ob/ob}$ mice was depleted using shRNA and observed a significant reduction in basal blood glucose concentrations compared to control. Importantly, reduced levels of PGC-1α in the liver blunted SR-18292-mediated reductions in blood glucose concentrations, indicating that PGC-1α contributes to the SR-18292 metabolic action (FIG. 23). To fully assess the effects of SR-18292 on whole body glucose homeostasis and insulin resistance, a glucose tolerance test (GTT) and insulin tolerance test (ITT) were performed following the same protocol used to determine fasting blood glucose. Interestingly, SR-18292 treatment significantly enhanced glucose tolerance both in DIO mice and Lep$^{ob/ob}$ mice (FIGS. 24 and 25). As expected, insulin levels after GTT were lower in the treated group (FIG. 51). In addition, the response to insulin was also enhanced in the drug treated group (FIG. 26), suggesting an improved response to insulin at the whole body level. To test if SR-18292 chronic treatment will cause similar anti-diabetic effects, mice were treated for a period of 14 days. The ability of SR-18292 to reduce blood glucose was sustained during this period without resulting in changes in body weight (FIGS. 57 and 58). Importantly, this longer treatment did not cause any signs of toxicity as measured by serum ALT and AST levels, H&E staining of liver slices and the expression of proinflammatory genes (FIGS. 59-61).

TABLE 6

Serum biochemistry parameters following treatment with SR-18292.

|  | Vehicle | SR-18292 (45 mg/kg) |
|---|---|---|
| ALT (U/L) | 7.87 (±1.57) | 9.21 (±3.64) |
| AST (U/L) | 30.82 (±1.23) | 29.94 (±2.25) |
| LDH (IU/L) | 86.18 (±12.39) | 64.44 (±8.39) |
| Bilirubin (mg/dL) | 0.43 (±0.08) | 0.33 (±0.39) |

Serum enzymatic activities of alanine transaminase (ALT), aspartate aminotransferase (AST), lactate dehydrogenase (LDH) and bilirubin levels from mice fed high fat diet and treated with SR-18292. n=7.

Figure 27:
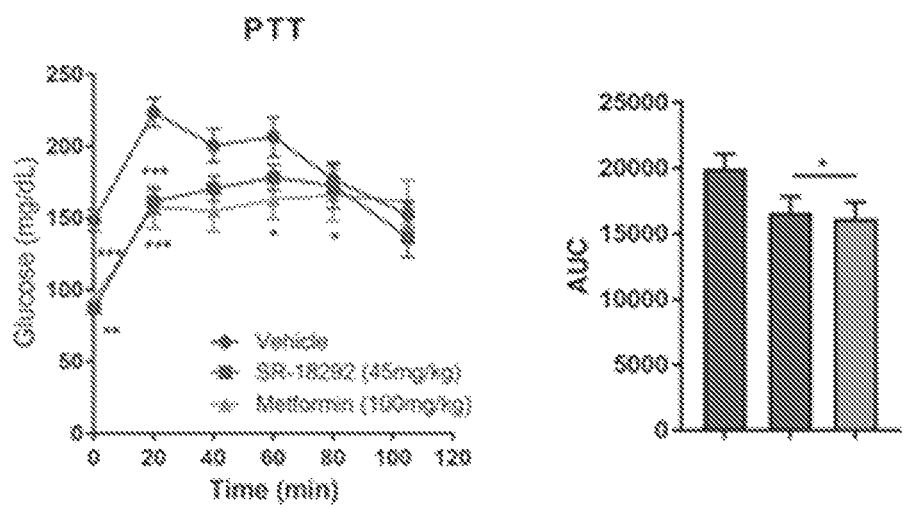
FIG. 27 depicts data showing PTT following treatment with SR-18292 and metformin in mice fed HFD for 17 weeks. n=10/vehicle, n=10/SR-18292, n=7/Metformin. Two-way ANOVA with Sidak posttest.
Figure 28:
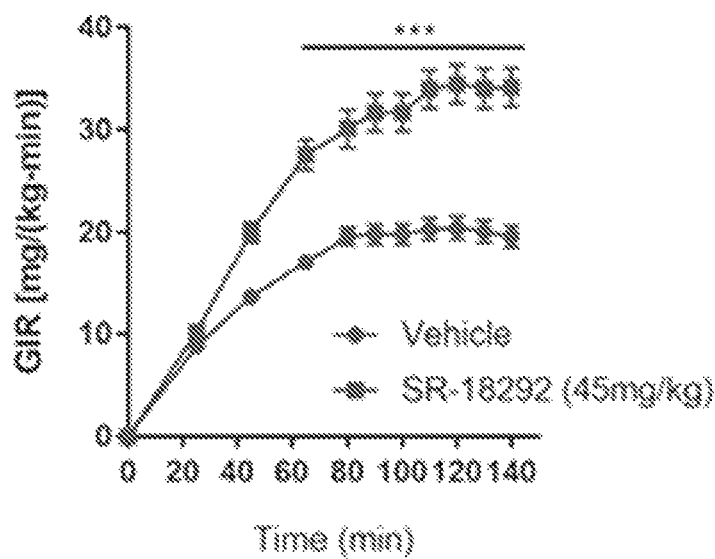
FIG. 28, FIG. 29, and FIG. 30 depict data showing the hyperinsulinemic euglycemic clamp studies from mice fed HFD for 16 weeks. Glucose infusion rate (GIR), glucose uptake and endogenous glucose production (EGP) are presented. n=9/vehicle, n=7/SR-18292.
Figure 29:
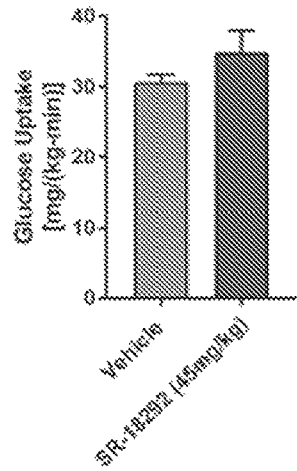
Figure 30:
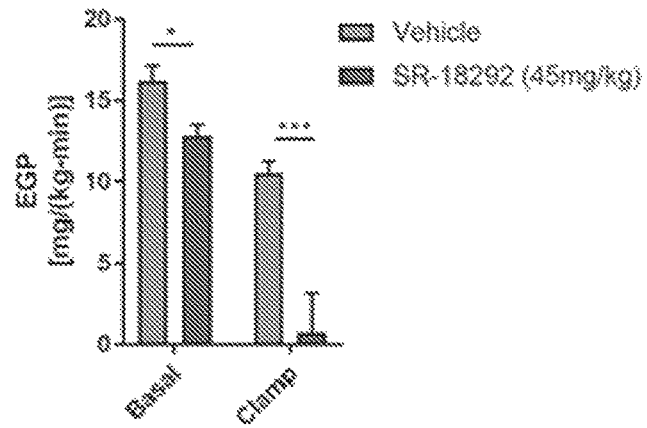
Figure 31:
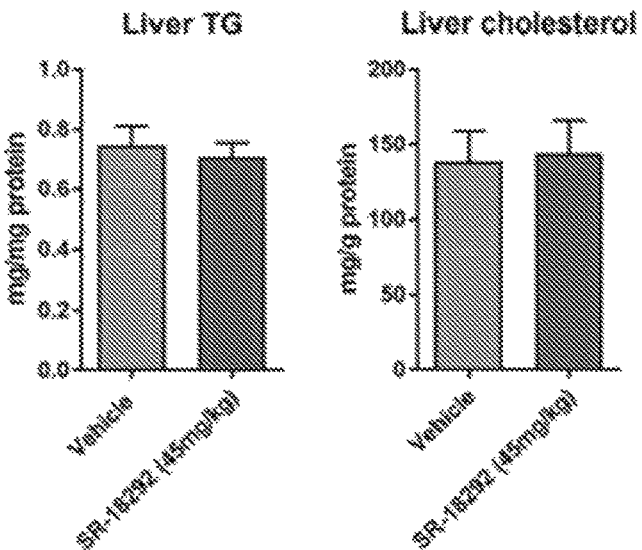
FIG. 31 is two bar graphs showing liver triglycerides and cholesterol levels from livers isolated from mice fed HFD for 17 weeks and treated with SR-18292. n=10. *$P<0.05$, $P<0.01$, *$P<0.001$. AUC, area under the curve.
Figure 52:
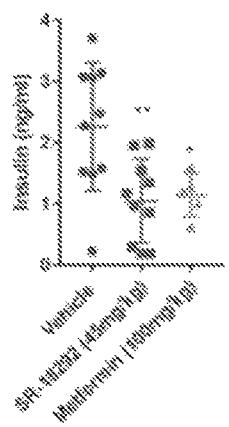
FIG. 52 is a plot showing the plasma insulin levels after PTT.
Figure 53:
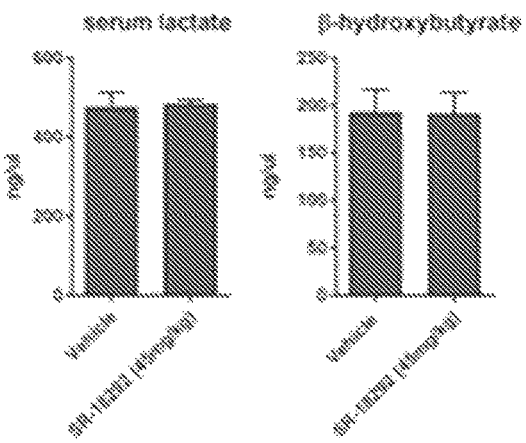
FIG. 53 is a bar graph showing that serum lactate and β-hydroxybutyrate levels are not altered with SR-18292 treatment. Mice were fed HFD for 4 weeks. n=7.
Figure 54:
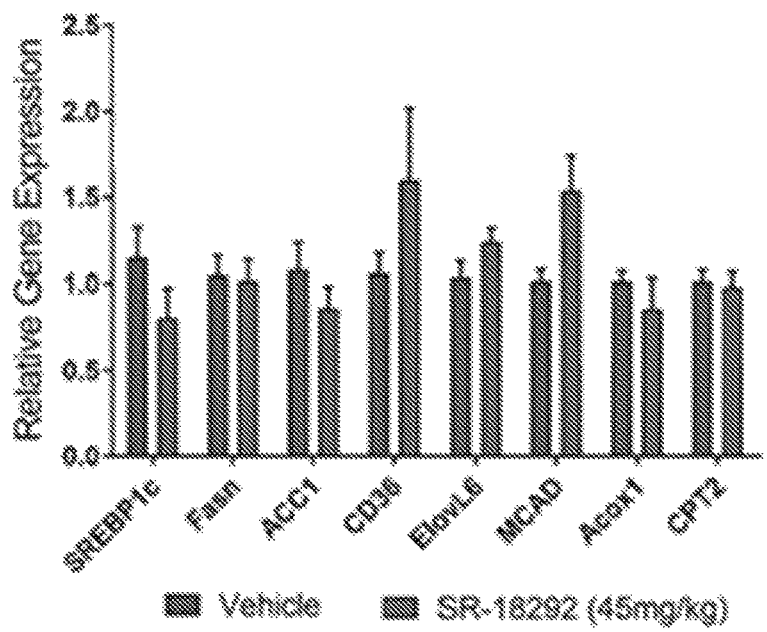
FIG. 54 depicts data showing that mRNA expression level of lipid metabolic genes is not changed with SR-18292 treatment. Mice were fed HFD for 13 weeks. n=10.
Figure 55:
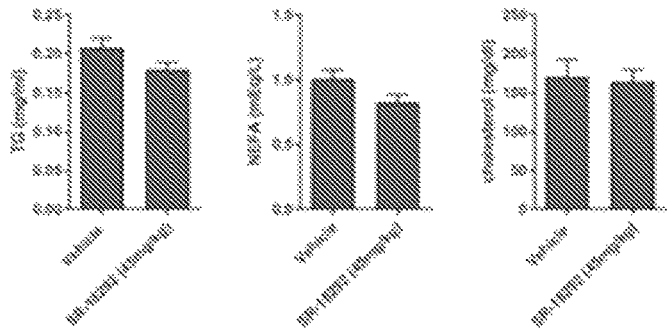
FIG. 55 is a series of bar graphs showing that Serum TG, free fatty acids and cholesterol levels are not altered with SR-18292 treatment. Mice were fed HFD for 13 weeks. NEFA, non-esterified fatty acids. n=10.
Figure 56:
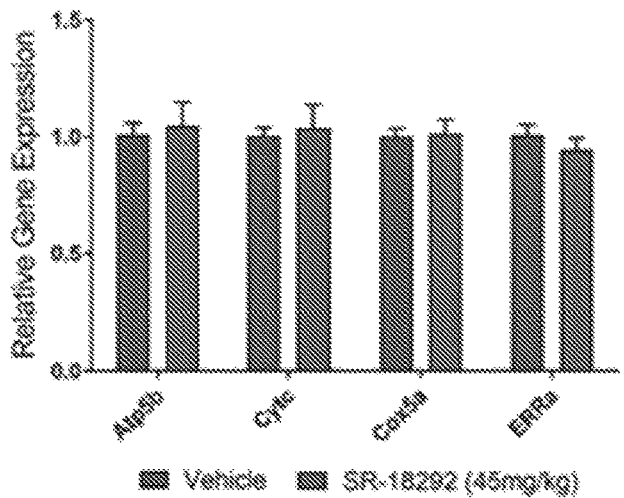
FIG. 56 is a bar graph showing mRNA expression level of mitochondrial genes in liver is not changed with SR-18292 treatment. Mice were fed HFD for 13 weeks. n=10.
Figure 62:
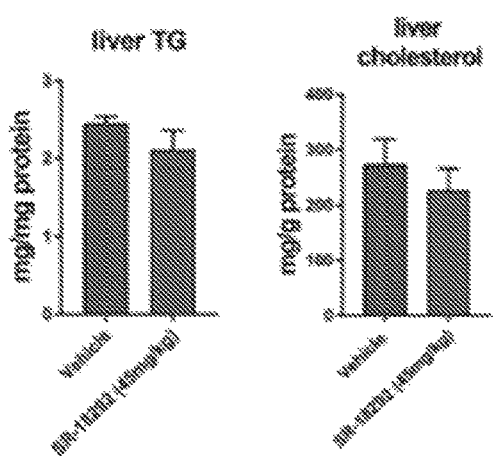
FIG. 62 is a bar graph showing Liver triglycerides and cholesterol levels are not altered after 14 days of SR-18292 treatment. n=10.
Figure 63:
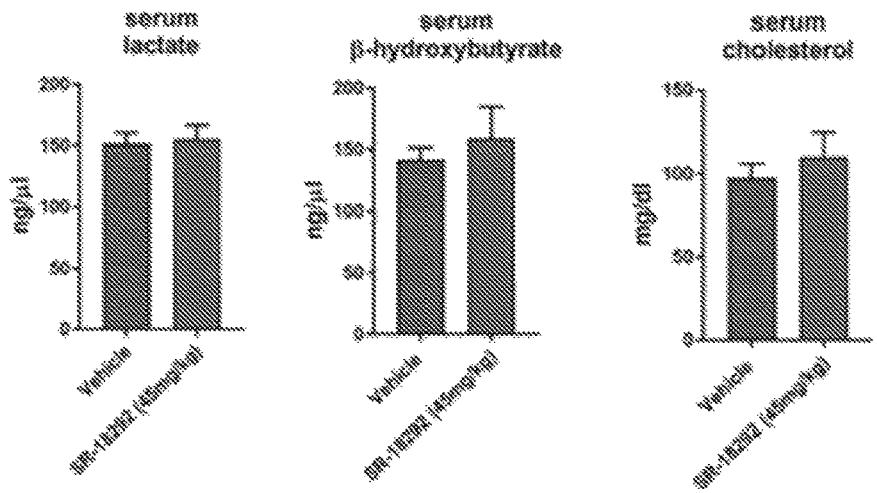
FIG. 63 is a bar graph showing Serum lactate, β-hydroxybutyrate and cholesterol levels are not altered after 14 days of SR-18292 treatment. n=10.
Figure 64:
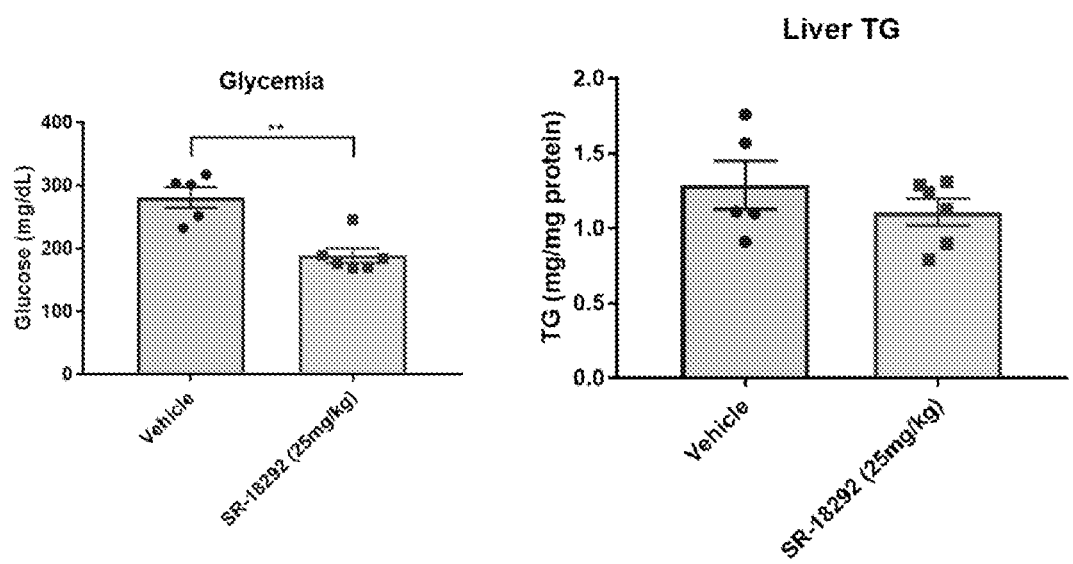
FIG. 64 depicts two bar graphs showing that SR-18292 improved fasting glycemia in diabetic leptin deficient ob/ob mice without altering lipid accumulation in liver.

Example 8—SR-18292 Suppresses HGP and Increases Liver Insulin Sensitivity In Vivo The strong effects of SR-18292 in primary hepatocytes prompted us to specifically test the ability of the liver to produce glucose upon treatment with SR-18292. To this end, a pyruvate tolerance test (PTT), in which pyruvate is injected to mice to increase HGP was performed. In accordance with the effects in isolated hepatocytes, glucose levels after pyruvate injection were significantly reduced in the SR-18292 treated group, suggesting that HGP from pyruvate is impaired as a result of the compound treatment (FIGS. 27 and 52). Interestingly, the defects in glucose production were comparable to that mediated by metformin treatment. To further analyze the cause of changes in blood glucose, hyperinsulinemic-euglycemic clamp studies were performed in HFD-fed mice treated with SR-18292. The glucose infusion rate in the SR-18292-treated mice was substantially higher compared to vehicle-treated mice (FIG. 28), reflecting the improved insulin sensitivity. Importantly, this was not due to improved peripheral glucose uptake (FIG. 29) but rather by reduced endogenous glucose production both under basal and clamp conditions (FIG. 30), further corroborating that SR-18292 improves hyperglycemia via reduction in HGP and strongly increases selective hepatic insulin sensitivity. Inhibition of HGP can result in a side effect in which carbons are diverted toward lipid synthesis, leading ultimately to accumulation of triglycerides (TG) and cholesterol in the liver causing hepatic steatosis. The treatment with SR-18292 did not cause this side effect, as liver TG and cholesterol levels were not changed even after prolonged treatment (FIGS. 31 and 62). Another concern associated with inhibition of gluconeogenesis is accumulation of lactate or ketone bodies in the blood that can lead to lactic- or keto-acidosis, respectively, a major concern in diabetes management. Treatment with SR-18292 is not likely to induce such an effect since both serum lactate and ketone bodies were not changed (FIGS. 53 and 63). The transcriptional lipid metabolic profile (FIG. 54), serum levels of TG, free fatty acids and cholesterol (FIG. 55) were not significantly altered with SR-18292 treatment. In addition, the expression level of mitochondrial genes, also targeted by PGC-1α was not changed, further showing the selectivity of SR-18292 toward inhibition of gluconeogenesis (FIG. 56). Collectively, these data define SR-18292 as a chemical scaffold that significantly improves overall glucose homeostasis and support the potential use of this compound as a drug treatment to control blood glucose levels in diabetic states. It also shows that selective chemical inhibition of PGC-1α gluconeogenic activity in hepatocytes is a feasible strategy to reduce fasting blood glucose and improve hyperglycemia in pre-clinical mouse models of T2D.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound having a structure of Formula I or a pharmaceutically acceptable salt thereof:

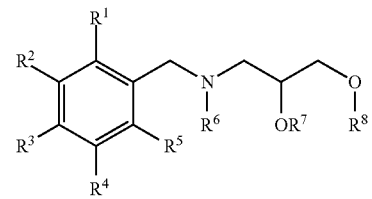

I wherein:
each of $R^1$, $R^2$, $R^4$, and $R^5$ is independently H, halo, optionally substituted alkyl, optionally substituted cycloalkyl or optionally substituted alkoxy;
$R^3$ is lower alkyl;
$R^6$ is optionally substituted alkyl or optionally substituted cycloalkyl;
$R^7$ is H or optionally substituted alkyl; and
$R^8$ is

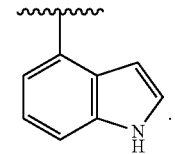 [SMILES: *c1cccc2[nH]ccc12]

2. The compound of claim 1, wherein $R^1$, $R^2$, $R^4$, and $R^5$ are independently H, halo, optionally substituted lower alkyl, or optionally substituted lower alkoxy.
3. The compound of claim 1, wherein $R^1$ is lower alkyl.
4. The compound of claim 1, wherein $R^2$ is lower alkyl.
5. The compound of claim 1, wherein $R^6$ is methyl, ethyl, n-propyl, iso-propyl, n-butyl, sec-butyl, tert-butyl, hexyl, pentyl, cyclopropyl, cyclobutyl cyclopentyl, or cyclohexyl.
6. The compound of claim 1, wherein $R^7$ is H.
7. The compound of claim 1, wherein the compound is selected from

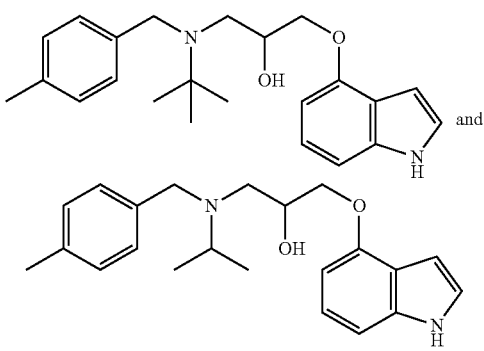

or a pharmaceutically acceptable salt thereof.

8. A pharmaceutical composition comprising a compound of claim 1 and a pharmaceutically acceptable carrier.

9. A method of treating or preventing a metabolic condition comprising administering to a subject a compound having a structure of Formula I or a pharmaceutically acceptable salt thereof:

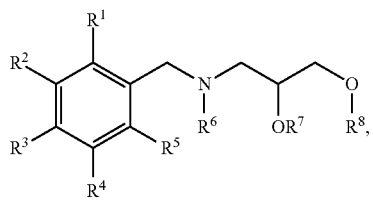

wherein:
each of $R^1$, $R^2$, $R^4$, and $R^5$ are independently H, halo, optionally substituted alkyl, optionally substituted cycloalkyl or optionally substituted alkoxy;
$R^3$ is lower alkyl;
$R^6$ is optionally substituted alkyl or optionally substituted cycloalkyl;
$R^7$ is H or optionally substituted alkyl; and
$R^8$ is

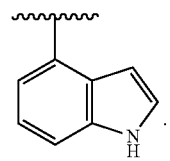 [SMILES: *c1cccc2[nH]ccc12]

or

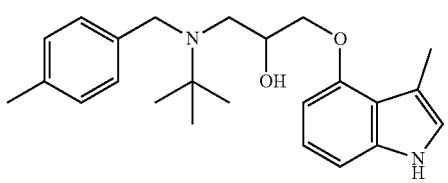 [SMILES: Cc1ccc(CN(CC(O)COc2cccc3[nH]cc(C)c23)C(C)(C)C)cc1]

or a pharmaceutically acceptable salt thereof.

10. The method of claim 9, further comprising conjointly administering an anti-diabetic drug to the subject.

11. A method of modulating glucose levels in a subject comprising administering to a subject a compound having a structure of Formula I or a pharmaceutically acceptable salt thereof:

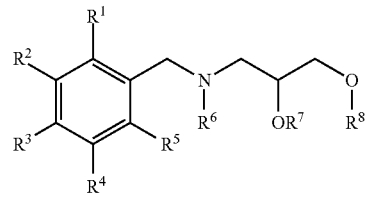

wherein:
each of $R^1$, $R^2$, $R^4$, and $R^5$ are independently H, halo, optionally substituted alkyl, optionally substituted cycloalkyl or optionally substituted alkoxy;
$R^3$ is lower alkyl;
$R^6$ is optionally substituted alkyl or optionally substituted cycloalkyl;
$R^7$ is H or optionally substituted alkyl; and
$R^8$ is

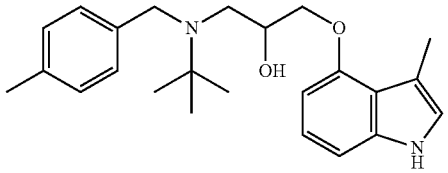 [SMILES: Cc1ccc(CN(CC(O)COc2cccc3[nH]cc(C)c23)C(C)(C)C)cc1]

or

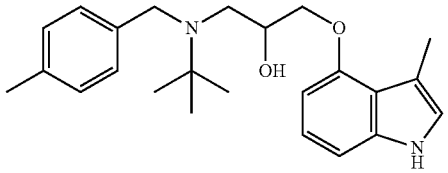 [SMILES: Cc1ccc(CN(CC(O)COc2cccc3[nH]cc(C)c23)C(C)(C)C)cc1]

or a pharmaceutically acceptable salt thereof.

12. The compound of claim 1, wherein at least one of $R^1$, $R^2$, $R^4$, and $R^5$ is not H.

13. The method of claim 9, wherein the method is a method of treating the metabolic condition.

* * * * *